United States Patent
Gefen et al.

(10) Patent No.: US 9,198,753 B2
(45) Date of Patent: Dec. 1, 2015

(54) TECHNIQUES FOR POWERING A RETINAL PROSTHESIS

(71) Applicant: NANO-RETINA INC., Wilmington, DE (US)

(72) Inventors: Ra'anan Gefen, Re'ut (IL); Yossi Gross, Moshav Mazor (IL); Tuvia Liran, Qiryat Tivon (IL); Shai Vaingast, Ganei Tikva (IL)

(73) Assignee: NANO-RETINA INC., Wilmington, DE (US)

( * ) Notice: Subject to any disclaimer, the term of this patent is extended or adjusted under 35 U.S.C. 154(b) by 0 days.

(21) Appl. No.: 14/199,462

(22) Filed: Mar. 6, 2014

(65) Prior Publication Data

US 2014/0188222 A1     Jul. 3, 2014

Related U.S. Application Data

(63) Continuation of application No. 13/437,310, filed on Apr. 2, 2012, now Pat. No. 8,706,243, which is a continuation-in-part of application No. 13/103,264, filed on May 9, 2011, now Pat. No. 8,442,641, and a (Continued)

(51) Int. Cl.
    *A61N 1/05*          (2006.01)
    *A61F 2/16*          (2006.01)
    (Continued)

(52) U.S. Cl.
    CPC .................. *A61F 2/1659* (2013.01); *A61F 2/14* (2013.01); *A61F 2/1624* (2013.01); *A61N 1/0543* (2013.01); *A61N 1/36046* (2013.01); *A61N 1/3787* (2013.01); *A61N 1/37217* (2013.01)

(58) Field of Classification Search
    CPC ....... A61F 2/1659; A61F 2/14; A61F 2/1624; A61N 1/0543
    USPC ............................................ 607/54, 139, 141
    See application file for complete search history.

(56) References Cited

U.S. PATENT DOCUMENTS

| 1,662,446 A | 3/1928 | Wappler |
| 2,721,316 A | 10/1955 | Shaw |

(Continued)

FOREIGN PATENT DOCUMENTS

| CA | 2235216 A1 | 4/1997 |
| CA | 2235316 | 4/1997 |

(Continued)

OTHER PUBLICATIONS

U.S. Appl. No. 13/148,461—Most Recent Claims Sheet.*

(Continued)

*Primary Examiner* — Christopher D Koharski
*Assistant Examiner* — Michael Carey
(74) *Attorney, Agent, or Firm* — Symbus Law Group, LLC; Clifford D. Hyra

(57) ABSTRACT

Apparatus for use with an external non-visible light source is provided. The apparatus comprises an intraocular device configured for implantation in a human eye, and comprising an energy receiver. The energy receiver is configured to receive light emitted from the external non-visible light source, and extract energy from the emitted light for powering the intraocular device. The intraocular device is configured to regulate a parameter of operation of the intraocular device based on a modulation of the light emitted by the external non-visible light source and received by the energy receiver. Other embodiments are also described.

13 Claims, 16 Drawing Sheets

Related U.S. Application Data continuation-in-part of application No. 12/852,218, filed on Aug. 6, 2010, now Pat. No. 8,428,740, and a continuation-in-part of application No. 12/687,509, filed on Jan. 14, 2010, now Pat. No. 8,718,784, and a continuation-in-part of application No. 12/368,150, filed on Feb. 9, 2009, now Pat. No. 8,150,526, and a continuation-in-part of application No. 13/148,461, filed as application No. PCT/IL2010/000097 on Feb. 3, 2010.

(51) Int. Cl.
*A61F 2/14* (2006.01)
*A61N 1/36* (2006.01)
*A61N 1/372* (2006.01)
*A61N 1/378* (2006.01)

(56) References Cited

U.S. PATENT DOCUMENTS

| | | |
|---|---|---|
| 2,760,483 A | 8/1956 | Tassicker |
| 4,197,850 A | 4/1980 | Schulman et al. |
| 4,262,294 A | 4/1981 | Hara et al. |
| 4,272,910 A | 6/1981 | Danz |
| 4,324,252 A | 4/1982 | Rossing et al. |
| 4,551,149 A | 11/1985 | Sciarra |
| 4,601,545 A | 7/1986 | Kern |
| 4,628,933 A | 12/1986 | Michelson |
| 4,664,117 A | 5/1987 | Beck |
| 4,786,818 A | 11/1988 | Mead et al. |
| 4,837,049 A | 6/1989 | Byers et al. |
| 4,903,702 A | 2/1990 | Putz |
| 4,914,738 A | 4/1990 | Oda et al. |
| 4,969,468 A | 11/1990 | Byers et al. |
| 5,016,633 A | 5/1991 | Chow |
| 5,024,223 A | 6/1991 | Chow |
| 5,081,378 A | 1/1992 | Watanabe |
| 5,108,427 A | 4/1992 | Majercik et al. |
| 5,109,844 A | 5/1992 | de Juan, Jr. et al. |
| 5,133,356 A | 7/1992 | Bryan et al. |
| 5,147,284 A | 9/1992 | Fedorov et al. |
| 5,159,927 A | 11/1992 | Schmid |
| 5,215,088 A | 6/1993 | Normann et al. |
| 5,314,458 A | 5/1994 | Najafi et al. |
| 5,397,350 A | 3/1995 | Chow et al. |
| 5,411,540 A | 5/1995 | Edell et al. |
| 5,476,494 A | 12/1995 | Edell et al. |
| 5,526,423 A | 6/1996 | Ohuchi et al. |
| 5,556,423 A | 9/1996 | Chow et al. |
| 5,575,813 A | 11/1996 | Edell et al. |
| 5,597,381 A | 1/1997 | Rizzo, III |
| 5,608,204 A | 3/1997 | Hofflinger et al. |
| 5,674,263 A | 10/1997 | Yamamoto et al. |
| 5,735,882 A | 4/1998 | Rottenberg et al. |
| 5,769,875 A | 6/1998 | Peckham et al. |
| 5,800,478 A | 9/1998 | Chen et al. |
| 5,800,533 A | 9/1998 | Eggleston et al. |
| 5,800,535 A | 9/1998 | Howard, III |
| 5,835,250 A | 11/1998 | Kanesaka |
| 5,836,996 A | 11/1998 | Doorish |
| 5,837,995 A | 11/1998 | Chow et al. |
| 5,865,839 A | 2/1999 | Doorish |
| 5,873,901 A | 2/1999 | Wu et al. |
| 5,895,415 A | 4/1999 | Chow et al. |
| 5,935,155 A | 8/1999 | Humayun et al. |
| 5,944,747 A | 8/1999 | Greenberg et al. |
| 5,949,064 A | 9/1999 | Chow et al. |
| 6,020,593 A | 2/2000 | Chow et al. |
| 6,032,062 A | 2/2000 | Nisch |
| 6,035,236 A | 3/2000 | Jarding et al. |
| 6,043,437 A | 3/2000 | Schulman et al. |
| 6,069,365 A | 5/2000 | Chow et al. |
| 6,075,251 A | 6/2000 | Chow et al. |
| 6,201,234 B1 | 3/2001 | Chow et al. |
| 6,230,057 B1 | 5/2001 | Chow et al. |
| 6,259,937 B1 | 7/2001 | Schulman et al. |
| 6,287,372 B1 | 9/2001 | Briand et al. |
| 6,298,270 B1 | 10/2001 | Nisch et al. |
| 6,324,429 B1 | 11/2001 | Shire et al. |
| 6,347,250 B1 | 2/2002 | Nisch et al. |
| 6,368,349 B1 | 4/2002 | Wyatt et al. |
| 6,389,317 B1 | 5/2002 | Chow et al. |
| 6,400,989 B1 | 6/2002 | Eckmiller |
| 6,427,087 B1 | 7/2002 | Chow et al. |
| 6,442,431 B1 | 8/2002 | Veraart et al. |
| 6,458,157 B1 | 10/2002 | Suaning |
| 6,472,122 B1 | 10/2002 | Schulman et al. |
| 6,473,365 B2 | 10/2002 | Joh et al. |
| 6,498,043 B1 | 12/2002 | Schulman et al. |
| 6,507,758 B1 | 1/2003 | Greenberg et al. |
| 6,533,798 B2 | 3/2003 | Greenberg et al. |
| 6,574,022 B2 | 6/2003 | Chow et al. |
| 6,611,716 B2 | 8/2003 | Chow et al. |
| 6,647,297 B2 | 11/2003 | Scribner |
| 6,658,299 B1 | 12/2003 | Dobelle |
| 6,677,225 B1 | 1/2004 | Ellis et al. |
| 6,678,458 B2 | 1/2004 | Ellis et al. |
| 6,683,645 B1 | 1/2004 | Collins et al. |
| 6,738,672 B2 | 5/2004 | Schulman et al. |
| 6,755,530 B1 | 6/2004 | Loftus et al. |
| 6,758,823 B2 | 7/2004 | Pasquale et al. |
| 6,761,724 B1 | 7/2004 | Zrenner et al. |
| 6,762,116 B1 | 7/2004 | Skidmore |
| 6,770,521 B2 | 8/2004 | Visokay et al. |
| 6,785,303 B1 | 8/2004 | Holzwarth et al. |
| 6,792,314 B2 | 9/2004 | Byers et al. |
| 6,804,560 B2 | 10/2004 | Nisch et al. |
| 6,821,154 B1 | 11/2004 | Canfield et al. |
| 6,844,023 B2 | 1/2005 | Schulman et al. |
| 6,847,847 B2 | 1/2005 | Nisch et al. |
| 6,888,571 B1 | 5/2005 | Koshizuka et al. |
| 6,904,239 B2 | 6/2005 | Chow et al. |
| 6,908,470 B2 | 6/2005 | Stieglitz et al. |
| 6,923,669 B1 | 8/2005 | Tsui et al. |
| 6,935,897 B2 | 8/2005 | Canfield et al. |
| 6,949,763 B2 | 9/2005 | Ovadia et al. |
| 6,961,619 B2 | 11/2005 | Casey |
| 6,970,745 B2 | 11/2005 | Scribner |
| 6,974,533 B2 | 12/2005 | Zhou |
| 6,976,998 B2 | 12/2005 | Rizzo et al. |
| 6,990,377 B2 | 1/2006 | Gliner et al. |
| 7,001,608 B2 | 2/2006 | Fishman et al. |
| 7,003,354 B2 | 2/2006 | Chow et al. |
| 7,006,873 B2 | 2/2006 | Chow et al. |
| 7,025,619 B2 | 4/2006 | Tsui et al. |
| 7,027,874 B1 | 4/2006 | Sawan et al. |
| 7,031,776 B2 | 4/2006 | Chow et al. |
| 7,035,692 B1 | 4/2006 | Maghribi et al. |
| 7,037,943 B2 | 5/2006 | Peyman |
| 7,047,080 B2 | 5/2006 | Palanker et al. |
| 7,058,455 B2 | 6/2006 | Huie, Jr. et al. |
| 7,071,546 B2 | 7/2006 | Fey et al. |
| 7,079,881 B2 | 7/2006 | Schulman et al. |
| 7,081,630 B2 | 7/2006 | Saini et al. |
| 7,096,568 B1 | 8/2006 | Nilsen et al. |
| 7,103,416 B2 | 9/2006 | Ok et al. |
| 7,107,097 B2 | 9/2006 | Stern et al. |
| 7,127,286 B2 | 10/2006 | Mech et al. |
| 7,127,301 B1 | 10/2006 | Okandan et al. |
| 7,130,693 B1 | 10/2006 | Montalbo |
| 7,133,724 B2 | 11/2006 | Greenberg et al. |
| 7,139,612 B2 | 11/2006 | Chow et al. |
| 7,147,865 B2 | 12/2006 | Fishman et al. |
| 7,149,586 B2 | 12/2006 | Greenberg et al. |
| 7,158,834 B2 | 1/2007 | Paul, Jr. |
| 7,158,836 B2 | 1/2007 | Suzuki |
| 7,160,672 B2 | 1/2007 | Schulman et al. |
| 7,162,308 B2 | 1/2007 | O'Brien et al. |
| 7,177,697 B2 | 2/2007 | Eckmiller et al. |
| 7,190,051 B2 | 3/2007 | Mech et al. |
| 7,191,010 B2 | 3/2007 | Ohta et al. |
| 7,224,300 B2 | 5/2007 | Dai et al. |
| 7,224,301 B2 | 5/2007 | Dai et al. |

(56) References Cited

U.S. PATENT DOCUMENTS

| | | |
|---|---|---|
| 7,235,350 B2 | 6/2007 | Schulman et al. |
| 7,242,597 B2 | 7/2007 | Shodo |
| 7,244,027 B2 | 7/2007 | Sumiya |
| 7,248,928 B2 | 7/2007 | Yagi |
| 7,251,528 B2 | 7/2007 | Harold |
| 7,255,871 B2 | 8/2007 | Huie, Jr. et al. |
| 7,257,446 B2 | 8/2007 | Greenberg et al. |
| 7,263,403 B2 | 8/2007 | Greenberg et al. |
| 7,271,525 B2 | 9/2007 | Byers et al. |
| 7,272,447 B2 | 9/2007 | Stett et al. |
| 7,291,540 B2 | 11/2007 | Mech et al. |
| 7,295,872 B2 | 11/2007 | Kelly et al. |
| 7,302,598 B2 | 11/2007 | Suzuki et al. |
| 7,314,474 B1 | 1/2008 | Greenberg et al. |
| 7,321,796 B2 | 1/2008 | Fink et al. |
| 7,342,427 B1 | 3/2008 | Fensore et al. |
| 7,377,646 B2 | 5/2008 | Suzuki |
| 7,379,000 B2 | 5/2008 | Dai et al. |
| 7,388,288 B2 | 6/2008 | Solzbacher et al. |
| 7,400,021 B2 | 7/2008 | Wu et al. |
| 7,447,547 B2 | 11/2008 | Palanker |
| 7,447,548 B2 | 11/2008 | Eckmiller |
| 7,480,988 B2 | 1/2009 | Ok et al. |
| 7,481,912 B2 | 1/2009 | Stelzle et al. |
| 7,482,957 B2 | 1/2009 | Dai et al. |
| 7,483,751 B2 | 1/2009 | Greenberg et al. |
| 7,493,169 B2 | 2/2009 | Greenberg et al. |
| 7,499,754 B2 | 3/2009 | Greenberg et al. |
| 7,539,544 B2 | 5/2009 | Greenberg et al. |
| 7,555,328 B2 | 6/2009 | Schulman et al. |
| 7,556,621 B2 | 7/2009 | Palanker et al. |
| 7,565,202 B2 | 7/2009 | Greenberg et al. |
| 7,565,203 B2 | 7/2009 | Greenberg et al. |
| 7,571,004 B2 | 8/2009 | Roy et al. |
| 7,571,011 B2 | 8/2009 | Zhou et al. |
| 7,574,263 B2 | 8/2009 | Greenberg et al. |
| 7,610,098 B2 | 10/2009 | McLean |
| 7,622,702 B2 | 11/2009 | Wu et al. |
| 7,630,771 B2 | 12/2009 | Cauller |
| 7,631,424 B2 | 12/2009 | Greenberg et al. |
| 7,638,032 B2 | 12/2009 | Zhou et al. |
| 7,666,523 B2 | 2/2010 | Zhou |
| 7,676,274 B2 | 3/2010 | Hung et al. |
| 7,691,252 B2 | 4/2010 | Zhou et al. |
| 7,706,887 B2 | 4/2010 | Tai et al. |
| 7,706,893 B2 | 4/2010 | Hung et al. |
| 7,709,961 B2 | 5/2010 | Greenberg et al. |
| 7,725,191 B2 | 5/2010 | Greenberg et al. |
| 7,734,352 B2 | 6/2010 | Greenberg et al. |
| 7,738,962 B2 | 6/2010 | Greenberg et al. |
| 7,749,608 B2 | 7/2010 | Laude et al. |
| 7,750,076 B2 | 7/2010 | Laude et al. |
| 7,751,896 B2 | 7/2010 | Graf et al. |
| 7,765,009 B2 | 7/2010 | Greenberg et al. |
| 7,766,903 B2 | 8/2010 | Blumenkranz et al. |
| 7,776,197 B2 | 8/2010 | Zhou |
| 7,831,309 B1 | 11/2010 | Humayun et al. |
| 7,834,767 B2 | 11/2010 | Shodo |
| 7,835,798 B2 | 11/2010 | Greenberg et al. |
| 7,840,273 B2 | 11/2010 | Schmid |
| 7,846,285 B2 | 12/2010 | Zhou et al. |
| 7,853,330 B2 | 12/2010 | Bradley et al. |
| 7,871,707 B2 | 1/2011 | Laude et al. |
| 7,877,866 B1 | 2/2011 | Greenberg et al. |
| 7,881,799 B2 | 2/2011 | Greenberg et al. |
| 7,887,681 B2 | 2/2011 | Zhou |
| 7,894,909 B2 | 2/2011 | Greenberg et al. |
| 7,894,911 B2 | 2/2011 | Greenberg et al. |
| 7,904,148 B2 | 3/2011 | Greenberg et al. |
| 7,908,011 B2 | 3/2011 | McMahon et al. |
| 7,912,556 B2 | 3/2011 | Greenberg et al. |
| 7,914,842 B1 | 3/2011 | Greenberg et al. |
| 7,937,153 B2 | 5/2011 | Zhou et al. |
| 7,957,811 B2 | 6/2011 | Caspi et al. |
| 7,962,221 B2 | 6/2011 | Greenberg et al. |
| 7,979,134 B2 | 7/2011 | Chow et al. |
| 7,989,080 B2 | 8/2011 | Greenberg et al. |
| 8,000,804 B1 | 8/2011 | Wessendorf et al. |
| 8,010,202 B2 | 8/2011 | Shah et al. |
| 8,010,206 B2 | 8/2011 | Dai et al. |
| 8,014,868 B2 | 9/2011 | Greenberg et al. |
| 8,014,869 B2 | 9/2011 | Greenberg et al. |
| 8,014,878 B2 | 9/2011 | Greenberg et al. |
| 8,024,022 B2 | 9/2011 | Schulman et al. |
| 8,034,229 B2 | 10/2011 | Zhou et al. |
| 8,046,078 B2 | 10/2011 | Greenberg et al. |
| 8,060,211 B2 | 11/2011 | Greenberg et al. |
| 8,060,216 B2 | 11/2011 | Greenberg et al. |
| 8,068,913 B2 | 11/2011 | Greenberg et al. |
| 8,078,284 B2 | 12/2011 | Greenberg et al. |
| 8,090,447 B2 | 1/2012 | Tano et al. |
| 8,090,448 B2 | 1/2012 | Greenberg et al. |
| 8,103,352 B2 | 1/2012 | Fried et al. |
| 8,121,697 B2 | 2/2012 | Greenberg et al. |
| 8,131,375 B2 | 3/2012 | Greenberg et al. |
| 8,131,378 B2 | 3/2012 | Greenberg et al. |
| 8,145,322 B1 | 3/2012 | Yao et al. |
| 8,150,526 B2 | 4/2012 | Gross et al. |
| 8,150,534 B2 | 4/2012 | Greenberg et al. |
| 8,160,713 B2 | 4/2012 | Greenberg et al. |
| 8,165,680 B2 | 4/2012 | Greenberg et al. |
| 8,170,676 B2 | 5/2012 | Greenberg et al. |
| 8,170,682 B2 | 5/2012 | Greenberg et al. |
| 8,180,453 B2 | 5/2012 | Greenberg et al. |
| 8,180,454 B2 | 5/2012 | Greenberg et al. |
| 8,180,460 B2 | 5/2012 | Nevsmith et al. |
| 8,190,267 B2 | 5/2012 | Greenberg et al. |
| 8,195,266 B2 | 6/2012 | Whalen, III et al. |
| 8,197,539 B2 | 6/2012 | Nasiatka et al. |
| 8,239,034 B2 | 8/2012 | Greenberg et al. |
| 8,244,362 B2 | 8/2012 | Yonezawa |
| 8,359,083 B2 | 1/2013 | Clark et al. |
| 8,428,740 B2 | 4/2013 | Gefen et al. |
| 2001/0011844 A1 | 8/2001 | Ernst et al. |
| 2002/0091421 A1 | 7/2002 | Greenberg et al. |
| 2003/0023297 A1 | 1/2003 | Byers et al. |
| 2003/0032946 A1 | 2/2003 | Fishman et al. |
| 2003/0100823 A1 | 5/2003 | Kipke et al. |
| 2003/0132946 A1 | 7/2003 | Gold |
| 2003/0181957 A1 | 9/2003 | Greenberg |
| 2003/0208248 A1 | 11/2003 | Carter et al. |
| 2004/0054407 A1 | 3/2004 | Tashiro et al. |
| 2004/0078064 A1 | 4/2004 | Suzuki |
| 2004/0080026 A1 | 4/2004 | Minamio et al. |
| 2004/0082981 A1* | 4/2004 | Chow et al. ............ 607/54 |
| 2004/0088026 A1 | 5/2004 | Chow et al. |
| 2004/0098067 A1 | 5/2004 | Ohta et al. |
| 2004/0181265 A1 | 9/2004 | Palanker et al. |
| 2004/0189940 A1 | 9/2004 | Kutschbach et al. |
| 2005/0015120 A1* | 1/2005 | Seibel et al. ............ 607/54 |
| 2005/0119605 A1 | 6/2005 | Sohn |
| 2005/0146954 A1 | 7/2005 | Win et al. |
| 2005/0168569 A1 | 8/2005 | Igarashi |
| 2006/0106432 A1 | 5/2006 | Sawan et al. |
| 2006/0111757 A9 | 5/2006 | Greenberg et al. |
| 2006/0184245 A1 | 8/2006 | Graf et al. |
| 2006/0256989 A1 | 11/2006 | Olsen et al. |
| 2006/0282128 A1 | 12/2006 | Tai et al. |
| 2006/0287688 A1 | 12/2006 | Yonezawa |
| 2007/0005116 A1 | 1/2007 | Lo |
| 2007/0123766 A1 | 5/2007 | Whalen et al. |
| 2007/0142877 A1 | 6/2007 | McLean |
| 2007/0142878 A1 | 6/2007 | Krulevitch et al. |
| 2007/0191909 A1 | 8/2007 | Ameri et al. |
| 2008/0114230 A1 | 5/2008 | Addis |
| 2008/0234791 A1 | 9/2008 | Arle et al. |
| 2008/0262571 A1 | 10/2008 | Greenberg et al. |
| 2008/0288036 A1 | 11/2008 | Greenberg et al. |
| 2008/0288067 A1 | 11/2008 | Flood |
| 2008/0294224 A1 | 11/2008 | Greenberg |
| 2009/0002034 A1 | 1/2009 | Westendorp et al. |
| 2009/0005835 A1 | 1/2009 | Greenberg et al. |
| 2009/0024182 A1 | 1/2009 | Zhang et al. |
| 2009/0118805 A1 | 5/2009 | Greenberg et al. |

(56) References Cited

U.S. PATENT DOCUMENTS

| | | | |
|---|---|---|---|
| 2009/0192571 | A1 | 7/2009 | Stett et al. |
| 2009/0204207 | A1 | 8/2009 | Blum et al. |
| 2009/0204212 | A1 | 8/2009 | Greenberg et al. |
| 2009/0216295 | A1 | 8/2009 | Zrenner et al. |
| 2009/0228069 | A1 | 9/2009 | Dai et al. |
| 2009/0287275 | A1 | 11/2009 | Suaning et al. |
| 2009/0326623 | A1 | 12/2009 | Greenberg et al. |
| 2010/0087895 | A1 | 4/2010 | Zhou et al. |
| 2010/0174224 | A1 | 7/2010 | Sohn |
| 2010/0204754 | A1 | 8/2010 | Gross |
| 2010/0249877 | A1 | 9/2010 | Naughton |
| 2010/0249878 | A1 | 9/2010 | McMahon et al. |
| 2010/0331682 | A1 | 12/2010 | Stein et al. |
| 2011/0054583 | A1 | 3/2011 | Litt et al. |
| 2011/0106229 | A1 | 5/2011 | Ortmann |
| 2011/0172736 | A1 | 7/2011 | Gefen et al. |
| 2011/0254661 | A1 | 10/2011 | Fawcett et al. |
| 2012/0035725 | A1 | 2/2012 | Gefen et al. |
| 2012/0035726 | A1 | 2/2012 | Gross |
| 2012/0041514 | A1 | 2/2012 | Gross et al. |
| 2012/0194781 | A1 | 8/2012 | Agurok |
| 2012/0209350 | A1 | 8/2012 | Taylor et al. |
| 2012/0221103 | A1 | 8/2012 | Liran et al. |
| 2012/0259410 | A1 | 10/2012 | Gefen et al. |
| 2012/0283800 | A1 | 11/2012 | Perryman et al. |
| 2013/0126713 | A1 | 5/2013 | Haas et al. |
| 2013/0322462 | A1 | 12/2013 | Poulsen |
| 2014/0031931 | A1 | 1/2014 | Liran et al. |
| 2014/0047713 | A1 | 2/2014 | Singh et al. |

FOREIGN PATENT DOCUMENTS

| | | | |
|---|---|---|---|
| CN | 1875895 | | 12/2006 |
| DE | 10315397 | | 10/2004 |
| DE | 10315397 | A1 | 10/2004 |
| JP | 2000-350742 | | 12/2000 |
| WO | WO0174444 | | 10/2001 |
| WO | WO0191854 | | 12/2001 |
| WO | WO03032946 | | 4/2003 |
| WO | WO2007009539 | | 1/2007 |
| WO | WO 2007/076347 | | 5/2007 |
| WO | WO2007095395 | | 8/2007 |
| WO | WO2010035173 | | 4/2010 |
| WO | WO2010089739 | | 8/2010 |
| WO | WO2011086545 | | 7/2011 |
| WO | WO 2011/163262 | A2 | 12/2011 |
| WO | 2012/017426 | | 2/2012 |
| WO | 2012/114327 | | 8/2012 |
| WO | WO 2012/114327 | | 8/2012 |
| WO | WO/2012/153325 | | 11/2012 |

OTHER PUBLICATIONS

Partial ISR dated Jun. 16, 2014 for PCT/IB2014/059672.
ISR and written opinion, dated Feb. 27, 2014, which issued in PCT/IB2013/060270.
Examination Report, dated Apr. 16, 2014, which issued during prosecution of EP11732733.8.
Official Action, dated Nov. 27 2013, which issued during prosecution of JP 2011-548843.
Examination Report, dated Feb. 26, 2014, which issued during prosecution of EP10738277.2.
Extended European Search Report, dated Nov. 19, 2013, which issued during the prosecution of European Patent Application No. 11814197.7.
J.F. Rizzo, "Methods and Perceptual Thresholds for Short-Term Electrical Stimulation of Human Retina with Microelectrode Arrays", Investigative Ophthalmology and Visual Science, vol. 44, No. 12, (Dec. 1, 2003) pp. 5355-5361.
Delbruck et al.: "Analog VLSI Adaptive, Logarithmic, Wide-Dynamic-Range Photoreceptor," 1994 International Symposium on Circuits and Systems (London, 1994), p. 339-342.
Grill W., at al., Implanted Neural Interfaces: Biochallenges and Engineered Solutions, Annu. Rev. Biomed. Eng. 2009, 11:1.
Jourdain R P., at al., "Fabrication of piezoelectric thick-film bimorph micro-actuators from bulk ceramics using batch-scale methods" Multi-Material Micro Manufacture, S. Dimov and W. Menz (Eds.) 2008 Cardiff University, Cardiff, UK., Whittles Publishing Ltd.
Kim B., "Through-Silicon-Via Copper Deposition for Vertical Chip Integration" Master. Res, Soc. Symp. Proc. vol. 970, 2007 Material Research Society.
Lianga C, at al., "Surface modification of cp-Ti using femtosecond laser micromachining and the deposition of Ca/P layer" Materials Letters vol. 62, Issue 23, Aug. 31, 2008, pp. 3783-3786—an abstract.
David C NG, et al., "Pulse frequency modulation based CMOS image sensor for subretinal stimulation" IEEE Transactions on Circuits and Systems-II: Express Briefs, vol. 53, No. 6, Jun. 2006.
News Release—Sony develops back-illuminated CMOS image sensor, realizing high picture quality, nearly twofold sensitivity (*1) and low noise, Jun. 2008 http://www.sony.net/SonyInfo/News/Press/200806/08-069E/index.html.
Puech M., et al., "Fabrication of 3D packaging TSV using DRIE" ALCATEL Micro Machining Systems, vvww.adixen.com, Mar. 2007.
Seo J M., et al., "Biocompatibility of polyimide microelectrode array for retinal stimulation," Materials Science and Engineering: C, vol. 24, No. 1, Jan. 5, 2004, pp. 185-189(5).
Sorkin R., et al., "Process entanglement as a neuronal anchorage mechanism to rough surfaces," Nanotechnology 20 (2009) 015101 (8pp).
Starzyk JA, et al., "A DC-DC charge pump design based on voltage doublers" IEEE Transaction on Circuits and Systems -I: Fundamental theory and applications, vol. 48, No. 3 Mar. 2001.
Stein DJ, et al., "High voltage with Si series photovoltaics" Proceedings of SPE, the International Society for Optical Engineering 2006, vol. 6287, pp. 62870D.1-62870D, (an abstract).
Swain P K., et al., "Back-Illuminated Image Sensors Come to the Forefront. Novel materials and fabrication methods increase quality and lower cost of sensors for machine vision and industrial imaging." Photonics Spectra Aug. 2008.
Vorobyeva A Y. at al., "Metallic light absorbers produced by femtosecond laser pulses," Advances in Mechanical Engineering vol. 2010, Article ID 452749, 4 pages doi:10.1155/2010/452749, Hindawi Publishing Corporation.
Vorobyeva A Y. et al., "Femtosecond laser structuring of titanium implants," Applied Surface Science vol. 253, Issue 17, Jun. 30, 2007, pp. 7272-7280—an abstract.
Wallman L., et al., "The geometric design of micromachined silicon sieve electrodes influences functional nerve regeneration," Biomaterials May 2001:22(10):1 187-93, (an abstract).
Walter P., et al., "Cortical Activation via an implanted wireless retinal prosthesis," Investigative Ophthalmology and Visual Science. 2005;46:1780-1785.
Wu J T. and Chang K L., "MOS charge pumps for low-voltage operation" IEEE Journal of Solid-State Circuits, vol. 33 No. 4 Apr. 1998.
Zrenner E., 2002. "Will retinal implants restore vision?" Science 295(5557), pp. 1022-1025.
Office Action dated Aug. 24, 2011 issued during the prosecution of related U.S. Appl. No. 12/368,150.
International Preliminary Report on Patentability and Written Opinion dated Aug. 9, 2011, issued in related International Application No. PCT/IL2010/000097.
International Search Report dated Aug. 17, 2010, issued in related International Application No. PCT/IL2010/000097.
International Search Report and Written Opinion dated Aug. 12, 2011, issued in related International Application No. PCT/IL2011/000022.
International Search Report and Written Opinion dated Dec. 12, 2011 issued in related International Application No. PCT/IL2011/00609.
An Office Action dated Aug. 28, 2012, which issued during the prosecution of U.S. Appl. No. 12/852,218.
An Office Action dated Sep. 28, 2012, which issued during the prosecution of U.S. Appl. No. 13/103,264.
An International Preliminary Report on Patentability dated Jul. 17, 2012, which issued during the prosecution of Applicant's PCT/IL2011/000022.

(56) References Cited

OTHER PUBLICATIONS

A Supplementary European Search Report dated Aug. 10, 2012, which issued during the prosecution of Applicant's European Application No. 10 73 8277.

Palanker D. et al., "Design of a high-resolution optoelectric retinal prosthesis". Journal of Neural Engineering, Institute of physics publishing, Bristol, GB. vol. 2, No. 1, Mar. 1, 2005, pp. S105-S120, XP002427333, ISSN: 17412552, DOI: 10.1088/1741-2560/2/1/012.

Cortical Visual Neuro-Prosthesis for the Blind: Retina-Like Software/Hardware Preprocessor, F.J. Pelayol, A. Martinezl, S. Romerol, Ch.A. Morillasl, E. Rosl , E. Fernandez2 1Dept. of Computer Architecture and Technology, University of Granada, Spain 2Dept. of Histology and Institute of Bioengineering, University Miguel Hernandez, Alicante, Spain Neural Engineering, 2003. Conference Proceedings. First International IEEE EMBS Conference.

"Single-Chip CMOS Image Sensors for a Retina Implant System", Markus Schwarz, Ralf Hauschild, Bedrich J. Hosticka, Senior Member, IEEE, Jurgen Huppertz, Student Member, IEEE, Thorsten Kneip, Member, IEEE, Stephan Kolnsberg, Lutz Ewe, and Hoc Khiem Trieu, 2000.

An International Search Report dated Aug. 12, 2011, which issued during the prosecution of Applicant s PCT/IL2011/000022.

An International Search Report and a Written Opinion both dated Sep. 17, 2012, which issued during the prosecution of Applicant's PCT/IL12/00057.

Schwarz et al. "Hardware Architecture of a Neural Net Based Retina Implant for Patients Suffering from Retinitis Pigmentosa," Fraunhofer Institute of Microelectronic Circuits and Systems, pp. 653-658 (1996).

Ganesan et al. "Diamond Penetrating Electrode Array for Epi-Retinal Prosthesis," 32nd Annual International Conference of the IEEE EMBS, pp. 6757-6760 (2010).

Finn, et al. "An Amphibian Model for Developing and Evaluating Retinal Protheses," 18th Annual International Conference of the IEEE Engineering in Medicine and Biology Society, pp. 1540-1541 (1996).

Shawn Kelly, "A System for Electrical Retinal Stimulation for Human Trials," Massachusetts Institute of Technology, pp. 1-45 (1998).

Andreou et al. "Analog Integrated Circuits and Signal Processing," An International Journal, vol. 9, No. 2, pp. 141-166 (1996).

Office Action for U.S. Appl. No. 13/034,516 dated Dec. 14, 2012.

Office Action for U.S. Appl. No. 12/687,509 dated Dec. 7, 2012.

Office Action for U.S. Appl. No. 13/148,461 dated Mar. 13, 2013.

Office Action for U.S. Appl. No. 12/687,509 dated Jun. 6, 2013.

International Search Report and Written Opinion for International Application No. PCT/IL2012/000186 dated Sep. 4, 2012.

Humayun et al. "Visual perception in a blind subject with a chronic microelectronic retinal prosthesis," Vision Research, vol. 43, pp. 2573-2581 (2003).

Tran et al. "A Fully Flexible Stimulator using 65 nm CMOS Process for 1024-electrode Epi-retinal Prosthesis," 31st Annual International Conference of the IEEE EMBS, pp. 1643-1646 (2009).

Office Action issued in U.S. Appl. No. 13/437,310, dated Aug. 12, 2013.

An interview summary in U.S. Appl. No. 13/437,310 dated Nov. 14, 2013 in connection with the Office Action issued on Aug. 12, 2013.

European Search Report for European Application No. EP11732733 dated Jul. 16, 2013.

Yoo et al. "Excimer laser deinsulation of Parylene-C on iridium for use in an activated iridium oxide film-coated Utah electrode array," Journal of Neuroscience Methods, 215 (2013) 78-87.

Official Action dated Oct. 22, 2013, which issued during the prosecution of Applicant's U.S. Appl. No. 13/148,461.

Normann et al., "High-resolution spatio-temporal mapping of visusal pathways using multi-electrode arrays," Vision Research 41 (2001) 1261-1275.

Notice of Allowance issued in U.S. Appl. No. 13/437,310, dated Jan. 28, 2014.

Office action that issued on Feb. 3, 2014 in U.S. Appl. No. 13/683,158.

Office action that issued on Mar. 3, 2015 in U.S. Appl. No. 13/148,461.

Office action that issued on Apr. 14, 2015 in U.S. Appl. No. 14/018,850.

Invitation to pay additional fees that issued in PCT/IB2014/067417.

Invitation to pay additional fees that issued in PCT/IB2015/050224.

EP search report dated Feb. 20, 2015 that issued in EP 12782462.1.

Partial International Search Report dated Mar. 31, 2015.

Partial International Search Report dated Mar. 24, 2015.

ISR and the Written Opinion issued on Jun. 30, 2015 in PCT/IB2014/067417.

ISR and the Written Opinion issued on Jun. 30, 2015 in PCT/IB2015/050224.

Office action that issued on Aug. 10, 2015 in U.S. Appl. No. 13/827,919.

Office action that issued on Aug. 20 in U.S. Appl. No. 14/160,314.

\* cited by examiner

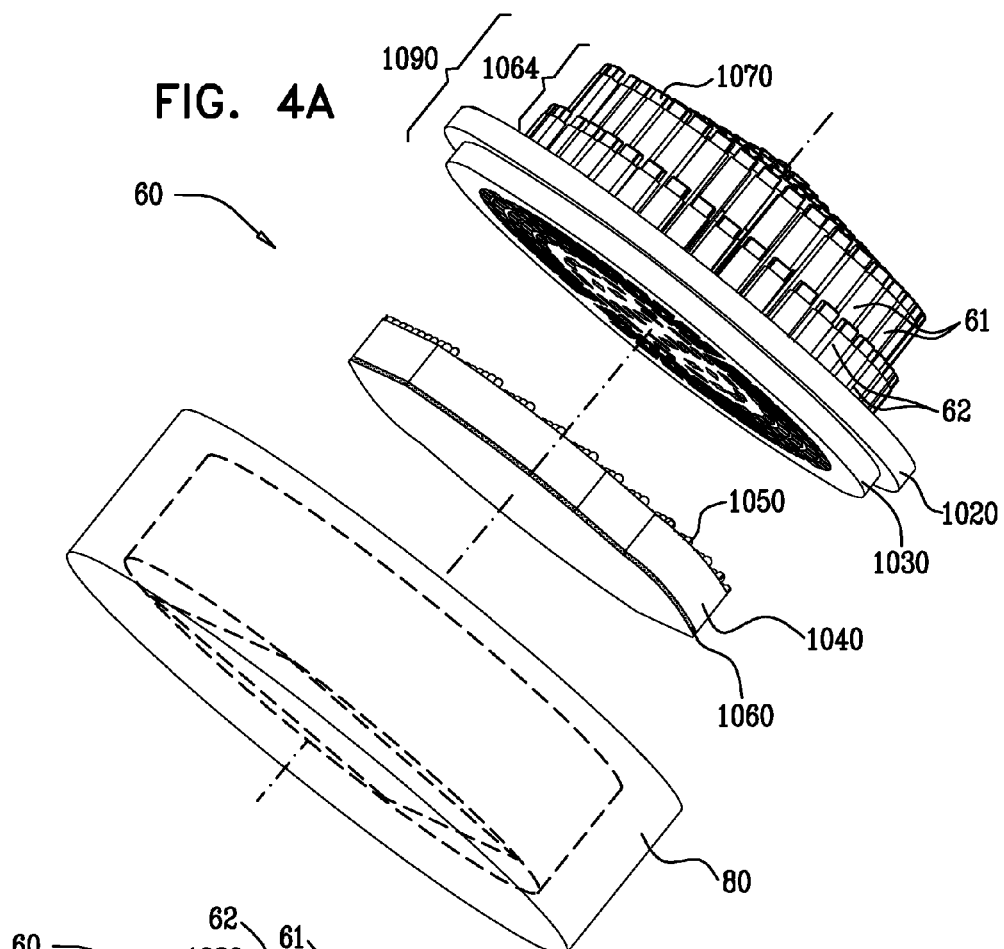
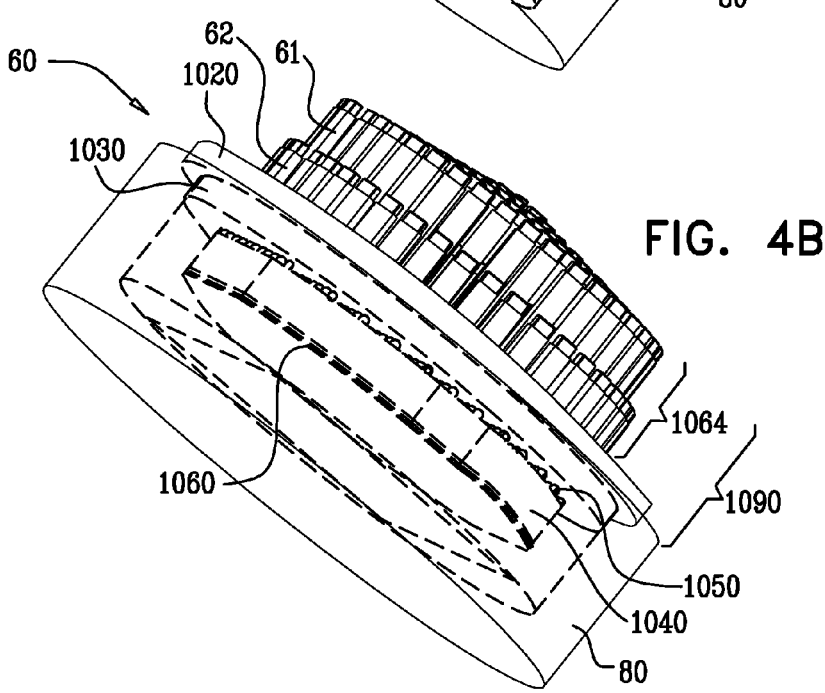

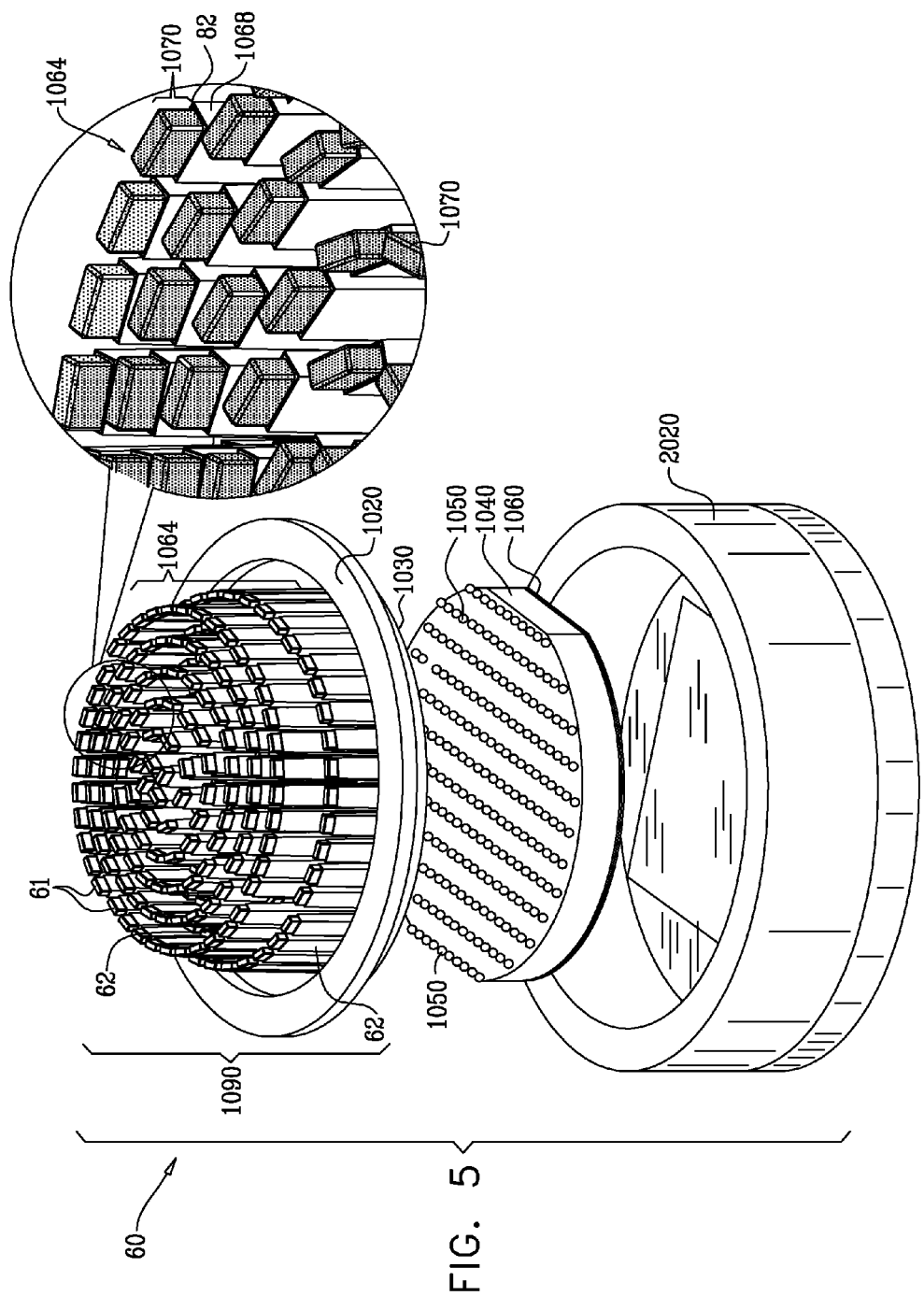

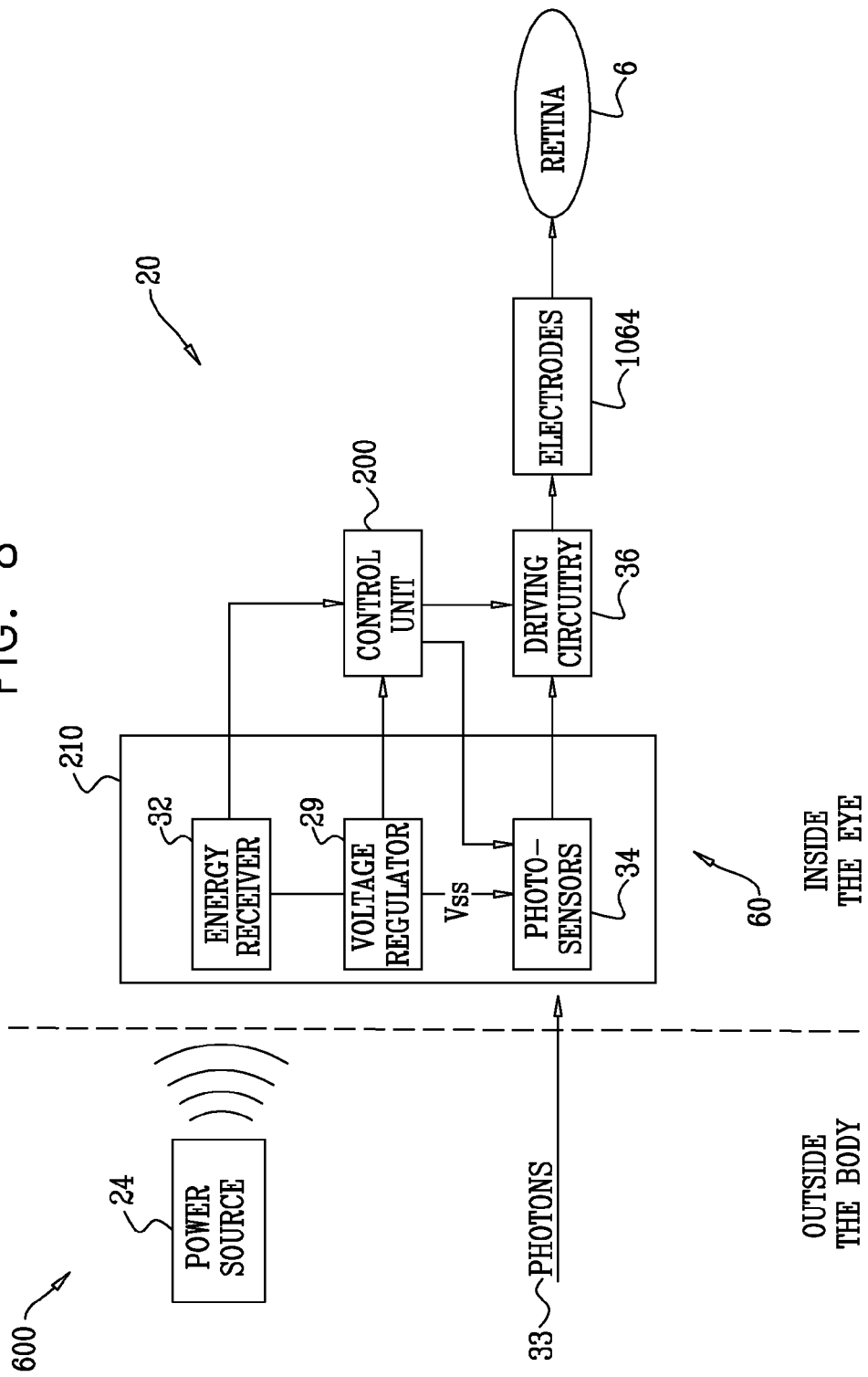

TECHNIQUES FOR POWERING A RETINAL PROSTHESIS

CROSS-REFERENCES TO RELATED APPLICATIONS

The present application is a continuation of U.S. Ser. No. 13/437,310 (US 2012/0259410 which issued as U.S. Pat. No. 8,706,243) to Gefen et al., which is a continuation-in-part of:

(a) U.S. Ser. No. 13/103,264 (US 2012/0035726 which issued as U.S. Pat. No. 8,442,641) to Gross et al., (b) U.S. Ser. No. 12/852,218 (US 2012/0035725 which issued as U.S. Pat. No. 8,428,740) to Gefen et al., (c) U.S. Ser. No. 12/687,509 (US 2011/0172736 which issued as U.S. Pat. No. 8,718,784) to Gefen et al., (d) U.S. Ser. No. 13/148,461 (US 2012/0041514) to Gross et al., which is the US national stage of PCT/IL2010/000097 (WO 2010/089739), and (e) U.S. Ser. No. 12/368,150 (US 2010/0204754 which issued as U.S. Pat. No. 8,150,526) to Gross et al.

All of the above-referenced applications are incorporated herein by reference.

FIELD OF EMBODIMENTS OF THE INVENTION

Some applications of the invention relate generally to implantable medical devices and more specifically to a retinal prosthesis.

BACKGROUND

Retinal malfunction, due to degenerative retinal diseases, is a leading cause of blindness and visual impairment. Implantation of a retinal prosthesis is a technology for restoring some useful vision in individuals suffering from retinal-related blindness.

The retina is a multi-layered light-sensitive structure that lines the posterior, inner part of the eye. The retina contains photoreceptor cells, for example rods and cones, which capture light and convert light signals into neural signals transmitted through the optic nerve to the brain. Rods are responsible for light sensitive, low resolution black and white vision, whereas cones are responsible for high resolution color vision. Most cones lie in the fovea, which defines the center of the retina. A bipolar cell layer exists between the photoreceptors and ganglion cells of the retina. The bipolar cell layer transmits signals from the photoreceptors to the ganglion cells whose axons form the optic nerve and transmit visual information to the brain.

SUMMARY OF APPLICATIONS OF THE INVENTION

In some applications of the present invention, a system is provided for restoring at least partial vision in a subject suffering from a retinal disease. The system comprises an apparatus comprising an external device, comprising a mount that is placed in front of the subject's eye. The mount may be, for example, a pair of eyeglasses. The external device further comprises a power source, for example a laser that is coupled to the mount and is configured to emit radiated energy that is outside the visible range directed toward the subject's eye.

The apparatus additionally comprises an intraocular device, which is implanted entirely in the subject's eye. The intraocular device comprises an intraocular retinal prosthesis, configured to be implanted in the subject's eye in either an epi-retinal or a sub-retinal position.

The intraocular device typically comprises a support substrate and an array of electrodes protruding from the support substrate. (In this context, in the specification and in the claims, "array" is meant to include rectangular as well as non-rectangular arrays (such as circular arrays). The protruding electrodes are shaped to define electrically-exposed tips which penetrate retinal tissue of the subject, bringing the electrodes in contact with the tissue. For some applications, a surface of the electrodes is treated to increase roughness and surface area of the electrodes, thus reducing electrode impendence and facilitating retinal stimulation and/or axon regeneration. Additionally or alternatively, the exposed tips of the electrodes have perforations passing therethrough, further increasing the surface area of the electrodes and allowing neuronal processes, to pass through and intertwine with the electrodes.

For some applications, the support substrate from which the electrodes protrude comprises additional elements of a retinal prosthesis, e.g., an energy receiving layer, a photosensor layer and driving circuitry that is powered by the energy receiving layer. The driving circuitry typically drives electrical charge into the retinal tissue from the tips of the electrodes, in response to sensing by the photosensor layer, in order to stimulate the retinal tissue.

For some applications, the photosensor layer is divided into units, each unit corresponding to a stimulating electrode in the array of electrodes.

The inventors have identified that, for some applications, sufficient stimulation of retinal tissue is a characteristic for consideration in enabling proper function of a retinal prosthesis. In particular, facilitating stimulation of the bipolar cell layer of the retina, which in turn stimulates ganglion cells, is a characteristic for consideration in retinal prosthesis provided by some applications of the present invention. The ganglion cells, whose axons form the optic nerve, further transmit the visual information to the brain resulting in the formation of an image. Penetrating perforated electrodes, in contrast to surface electrodes known in the art which sit on the surface of tissue, are configured to extend from either an epi-retinal or a sub-retinal implantation site and penetrate retinal tissue to directly contact and drive electrical charge into the bipolar cell layer from typically less than 10 um from the nearest bipolar cell. Rough electrode surfaces and perforations passing through the electrodes allow neuronal processes to grow therethrough, further improving cell-electrode coupling and increasing stimulation. Increased and direct contact of the retinal tissue by penetrating perforated electrodes enhances stimulation of the retina resulting in enhanced image resolution.

There is therefore provided in accordance with some applications of the present invention, apparatus for use with an external non-visible light source, the apparatus including:

an intraocular device configured for implantation in a human eye, and including an energy receiver configured to:
  receive light emitted from the external non-visible light source, and
  extract energy from the emitted light for powering the intraocular device, the intraocular device is configured to regulate a parameter of operation of the intraocular device based on a modulation of the light emitted by the external non-visible light source and received by the energy receiver.

For some applications, the intraocular device is configured to regulate the parameter of operation of the intraocular device based on amplitude modulation of the light emitted by the external non-visible light source and received by the energy receiver.

For some applications, the intraocular device is configured to regulate the parameter of operation of the intraocular device based on the amplitude modulation of the light, the modulation of the light varying between a minimum signal level and a maximum signal level, the minimum signal level being at least 20% of the maximum signal level.

For some applications, the intraocular device is configured to regulate the parameter of operation of the intraocular device based on the amplitude modulation of the light, the minimum signal level being at least 50% of the maximum signal level.

For some applications, the intraocular device is configured to regulate the parameter of operation of the intraocular device based on the amplitude modulation of the light, the modulation of the light being based on a carrier frequency of the modulated light being between 10 kHz and 100 kHz.

For some applications, the intraocular device is configured to regulate the parameter of operation of the intraocular device based on the amplitude modulation of the light, the light being received by the intraocular device in pulses having a pulse width of 1-10 usec.

For some applications, the external non-visible light source includes a sensor configured to sense a level of ambient light, the external non-visible light source modulating the light emitted by the external non-visible light source based on the level of ambient light, and the energy receiver is configured to receive ambient light and the light emitted from the external non-visible light source and to regulate the parameter of operation of the intraocular device based on amplitude modulation of the light.

For some applications, the energy receiver is configured to receive ambient light and the light emitted from the external non-visible light source, and the apparatus further includes a filter associated with the energy receiver, and configured to reduce a level of the ambient light from reaching the energy receiver.

For some applications, the energy receiver is configured to receive ambient light and the light emitted from the external non-visible light source, the modulation of the light varying between a minimum signal level and a maximum signal level, the minimum signal level being at least 20% of a summed strength of the received light emitted from the external non-visible light source and the received ambient light.

For some applications, the energy receiver is configured to receive the light emitted from the external non-visible light source and the ambient light, the minimum signal level being at least 50% of the summed strength of the received light emitted from the external non-visible light source and the received ambient light.

For some applications, the intraocular device is configured to regulate the parameter of operation of the intraocular device based on frequency modulation of the light emitted by the external non-visible light source and received by the energy receiver.

For some applications, the intraocular device is configured to regulate the parameter of operation of the intraocular device based on the frequency modulation of the light, the modulation of the light being based on a carrier wave having a frequency between 10 kHz and 100 kHz.

For some applications, the intraocular device is configured to regulate the parameter of operation of the intraocular device based on the frequency modulation of the light, the light being received by the intraocular device in pulses having a pulse width of 1-10 usec.

For some applications, the non-visible light source is configured to emit light that is outside of 380-750 nm and the intraocular device is configured to receive the light that is outside of 380-750 nm.

For some applications, the parameter of operation includes an intensity of the electrical current applied to the retina, and the apparatus is configured to regulate the intensity of the electrical current applied to the retina, based on the modulated light.

For some applications, the apparatus includes driving circuitry, and the energy receiver is configured to extract energy from the emitted light, for powering the intraocular device, and, the apparatus is configured, while extracting the energy, to receive ambient light and, responsively, transmit a signal to the driving circuitry.

For some applications, the energy receiver is configured to receive the ambient light and to transmit the signal to the driving circuitry.

For some applications, the apparatus includes driving circuitry, and the energy receiver is configured to extract energy from the emitted light, for powering the intraocular device, and, the apparatus is configured, during periods which alternate with the extracting of the energy, to receive ambient light and, responsively, transmit a signal to the driving circuitry.

For some applications, the energy receiver is configured to receive the ambient light and to transmit the signal to the driving circuitry.

For some applications, the intraocular device is configured to demodulate the modulated energy and, in response, regulate the operation parameter of the intraocular device.

There is further provided, in accordance with some applications of the present invention, an external device for association with an intraocular implant, the device including:

a power source including a modulator, the power source configured to emit non-visible light to the implant for transmitting power to the implant when the implant is located in the eye, the emitted light being modulated with a coded signal, such that, when the light is transmitted to the implant, the implant receives power and is controlled by the coded signal.

For some applications, the power source is configured to modulate the light with the coded signal using amplitude modulation of the light emitted by the power source.

For some applications, the power source is configured to modulate the light to vary between a minimum signal level and a maximum signal level, and the minimum signal level is at least 20% of the maximum signal level.

For some applications, power source is configured to set the minimum signal level to be at least 50% of the maximum signal level.

For some applications, the power source is configured to set a carrier frequency of the modulated light to be between 10 kHz and 100 kHz.

For some applications, the power source is configured to set a pulse width of pulses of the light to be 1-10 usec.

For some applications, the modulator is configured to modulate the light emitted from the power source between a minimum signal level and a maximum signal level, the minimum signal level being at least 20% of a summed strength of the light emitted from the power source and ambient light.

For some applications, the modulator is configured to modulate the light emitted from the power source to be at least 50% of the summed strength of the light emitted from power source and the ambient light.

For some applications the external device includes a sensor configured to sense a level of the ambient light, the modulator is configured to modulate the light emitted by the power source based on the level of ambient light.

For some applications, the power source is configured to set a wavelength of the emitted light to be outside of 380-750 nm.

For some applications, the power source is configured to emit the light and to not include image information in the emitted light.

For some applications, the modulator is configured to control a pulse frequency of electrical current applied to the retina by the implant, by modulating the emitted light with the coded signal.

For some applications the external device includes a mount that is coupled to the power source and is configured to be placed in front of an eye of a subject.

For some applications, the mount includes a pair of eyeglasses.

For some applications the external device includes a partially-transparent mirror coupled to the mount and configured to direct the non-visible light to the implant.

For some applications, the partially-transparent mirror is configured to allow ambient light to pass through to the implant.

There is still further provided, in accordance with some applications of the present invention, an intraocular device configured to be implanted entirely in a subject's eye, the intraocular device including:
a plurality of photosensors configured to receive an ambient image through a lens of the eye; and
an energy receiver configured to receive non-visible light through the lens of the eye and to extract power from the light for powering the photosensors,
the energy receiver is adapted to receive the light while the plurality of photosensors receive the ambient image.

For some applications, the energy receiver is additionally configured to receive visible light.

There is additionally provided, in accordance with some applications of the present invention, an intraocular implant, including:
a photosensor array adapted for implantation in a human eye;
an energy receiver adapted for implantation in the human eye and further adapted to receive a power signal in the form of a non-visible light beam; and
a filter associated with the photosensor array, configured to substantially prevent the power signal from reaching the photosensor array.

For some applications, the energy receiver is additionally configured to receive visible light.

For some applications, the photosensor array is configured to receive visible light, and the intraocular device further includes a filter associated with the energy receiver, configured to reduce a level of ambient light that reaches the energy receiver.

There is yet additionally provided, in accordance with some applications of the present invention, apparatus including:
an intraocular device, including at least one receiver configured for implantation in a human eye, the at least one receiver having an image reception portion and an energy reception portion configured to receive a power signal from a non-visible light beam; and
at least one control unit configured to prevent reception of at least a portion of the power signal by the image reception portion.

For some applications, the control unit is configured for implantation in the eye.

For some applications the apparatus includes a mount that is configured to be placed in front of the eye of the subject, and the control unit is coupled to the mount.

For some applications, the control unit is configured to prevent energy reception by the image reception portion, by sending a control signal to terminate the power signal.

For some applications the apparatus includes a filter, the control unit is configured to prevent energy reception by sending a control signal to activate the filter.

For some applications, the control unit is configured to prevent energy reception, by sending a control signal to deactivate the image reception portion.

For some applications, the energy reception portion is additionally configured to receive visible light.

There is still additionally provided, in accordance with some applications of the present invention, an intraocular device configured for epi-retinal implantation in a subject's eye, and configured for use with a plurality of photosensors, each photosensor configured to detect ambient photons and to generate a signal in response thereto, the intraocular device including:
a plurality of stimulating electrodes configured to penetrate a retinal layer of the subject's eye; and
driving circuitry, coupled to the photosensors, and configured to drive the electrodes to apply electrical pulses to a retina of the eye in response to the signal from the photosensors,
the driving circuitry is configured to vary a frequency of the pulses based on intensity of the ambient photons received by the photosensors.

For some applications, the intraocular device includes the plurality of photosensors.

For some applications, the driving circuitry is further configured to vary a parameter of the electrical pulses selected from the group consisting of: a number of the pulses, duration of each pulse, and a pulse repetition interval of the pulses.

For some applications, the driving circuitry is configured to reduce sub-harmonics by jittering the pulse frequency.

There is also provided, in accordance with some applications of the invention, an apparatus including:
an external device including:
    a mount, configured to be placed in front of an eye of a subject;
    a laser coupled to the mount and configured to emit radiation that is outside of 380-750 nm; and
    a partially-transparent mirror coupled to the mount; and
an intraocular device configured to be implanted entirely in the subject's eye, the intraocular device including:
    an energy receiver, configured to receive the radiation from the laser and to
    generate a voltage drop in response thereto;
    a plurality of stimulating electrodes;
    a plurality of photosensors, each photosensor configured to detect photons and
    to generate a signal in response thereto; and
    driving circuitry, coupled to the energy receiver and to the photosensors, and configured to receive the signals from the photosensors and to utilize the voltage drop to drive the electrodes to apply currents to a retina of the eye in response to the signals from the photosensors.

In some applications, the laser is configured to emit the light at 790-850 nm.

In some applications, the laser is configured to emit the light at 250-380 nm.

In some applications, the energy receiver is configured to receive light at 790-850 nm and to generate the voltage drop in response thereto.

In some applications, the energy receiver is configured to receive light at 250-380 nm and to generate the voltage drop in response thereto.

In some applications, the photosensors are generally insensitive to the energy from the laser.

In some applications, photosensors are generally sensitive to visible light.

In some applications, the energy receiver is configured to receive visible and non visible light, and to generate the voltage drop in response thereto.

In some applications, the intraocular device includes a filter configured to allow transmission to the photosensors of visible light only.

In some applications, the intraocular device includes a plurality of microlenses coupled to the energy receiver, facilitating refraction of visible light toward the photosensors.

In some applications, the intraocular device includes extending elements configured to provide anchoring of the intraocular device to the eye of the subject.

In some applications, the intraocular device includes extending elements to facilitate dissipation of heat away from at least the energy receiver.

In some applications, the electrodes include bipolar nanotube electrodes.

In some applications, the electrodes include monopolar nanotube electrodes.

In some applications, the electrodes include needle electrodes having exposed tips.

In some applications, the plurality of stimulating electrodes includes at least 100 electrodes.

In some applications, the intraocular device is configured to be implanted in an epi-retinal position.

In some applications, the intraocular device is configured to be implanted in a sub-retinal position.

In some applications, the apparatus includes a control element configured to receive an input from the subject, the external device is configured to modulate the energy emitted from the laser in response to the input, and the driving circuitry is configured to regulate a parameter of operation of the driving circuitry in response to the modulation of the energy emitted from the laser.

In some applications, the driving circuitry is configured to control an amount of stimulation per unit time applied by the electrodes, by the regulating of the parameter by the driving circuitry.

In some applications, the driving circuitry is configured to control an amplitude of the currents applied by the electrodes, by the regulating of the parameter by the driving circuitry.

In some applications, the driving circuitry is configured to control a sensitivity of the photosensors, by the regulating of the parameter by the driving circuitry.

In some applications, the external device includes a sensor coupled to the mount, configured to detect when an eyelid of the subject is closed, and the laser is configured to discontinue emission of the radiation when the eyelid is closed.

In some applications, the mount includes a filter configured to prevent transmission to the photosensors of ambient non-visible light.

In some applications, the filter includes a Schott filter.

In some applications, the driving circuitry is disposed in a single area of the intraocular device, and is configured to drive all of the electrodes.

In some applications, the apparatus includes a plurality of driving circuitries, each driving circuitry configured to drive a respective subset of electrodes.

In some applications, the plurality of driving circuitries includes 10-300 driving circuitries.

In some applications, the plurality of driving circuitries includes 300-3000 driving circuitries.

There is further provided in accordance with some applications of the invention apparatus, including:
an external device, including:
a mount, configured to be placed in front of an eye of a subject; and
a laser coupled to the mount and configured to emit radiation that is outside of 380-750 nm; and
an intraocular device configured to be implanted entirely in the subject's eye, the intraocular device including:
an energy receiver, configured to receive the radiation from the laser and to generate a voltage drop in response thereto;
a plurality of stimulating electrodes;
a plurality of photosensors, each photosensor configured to detect photons and to generate a signal in response thereto; and
driving circuitry, coupled to the energy receiver and to the photosensors, and configured to receive the signals from the photosensors and to utilize the voltage drop to drive the electrodes to apply currents to a retina of the eye in response to the signals from the photosensors,
and the external device is configured to modulate the radiation emitted from the laser, and the driving circuitry is configured to regulate a stimulation parameter of operation of the driving circuitry in response to the modulation of the radiation emitted from the laser.

In some applications, the driving circuitry is configured to drive the electrodes to apply the currents in pulses of current, and the stimulation parameter is selected from the group consisting of: a number of the pulses, a frequency of the pulses, a duration of each pulse, and a pulse repetition interval of the pulses.

There is additionally provided in accordance with some applications of the invention, a method for supplying power to a retinal implant, including:
emitting radiation from a laser, in a direction that is not toward the implant; and
receiving the radiation from the laser, by the implant.

In some applications, emitting the radiation comprises causing the radiation to be redirected toward the implant by a partially-transparent mirror.

There is yet further provided in accordance with some applications of the invention, a method for modulating stimulation parameters of an implant configured for implantation in a subject, the method including:
emitting laser radiation, from a laser to the implant;
receiving an input from the subject, and in response to receiving the input from the subject, modulating the radiation emitted from the laser; and
regulating a stimulation parameter of driving circuitry of the implant in response to the modulation of the radiation emitted from the laser.

In some applications, regulating the stimulation parameter includes:
driving currents into electrodes of the implant in pulses; and
in response to the modulation of the radiation, regulating at least one parameter selected from the group consisting of: a number of the pulses, a frequency of the pulses, a duration of each pulse, and a pulse repetition interval of the pulses.

The present invention will be more fully understood from the following detailed description of embodiments thereof, taken together with the drawings, in which:

BRIEF DESCRIPTION OF THE DRAWINGS

FIGS. 4A-B are schematic illustrations of an intraocular device for retinal stimulation, in accordance with some applications of the present invention;

FIG. 5 is a schematic illustration of an intraocular device for retinal stimulation, in accordance with some applications of the present invention;

FIG. 8 is a block diagram of the transmission of energy, information, and instructions, in the system for restoring vision, in accordance with some applications of the present invention;

DETAILED DESCRIPTION OF EMBODIMENTS

Figure 1:
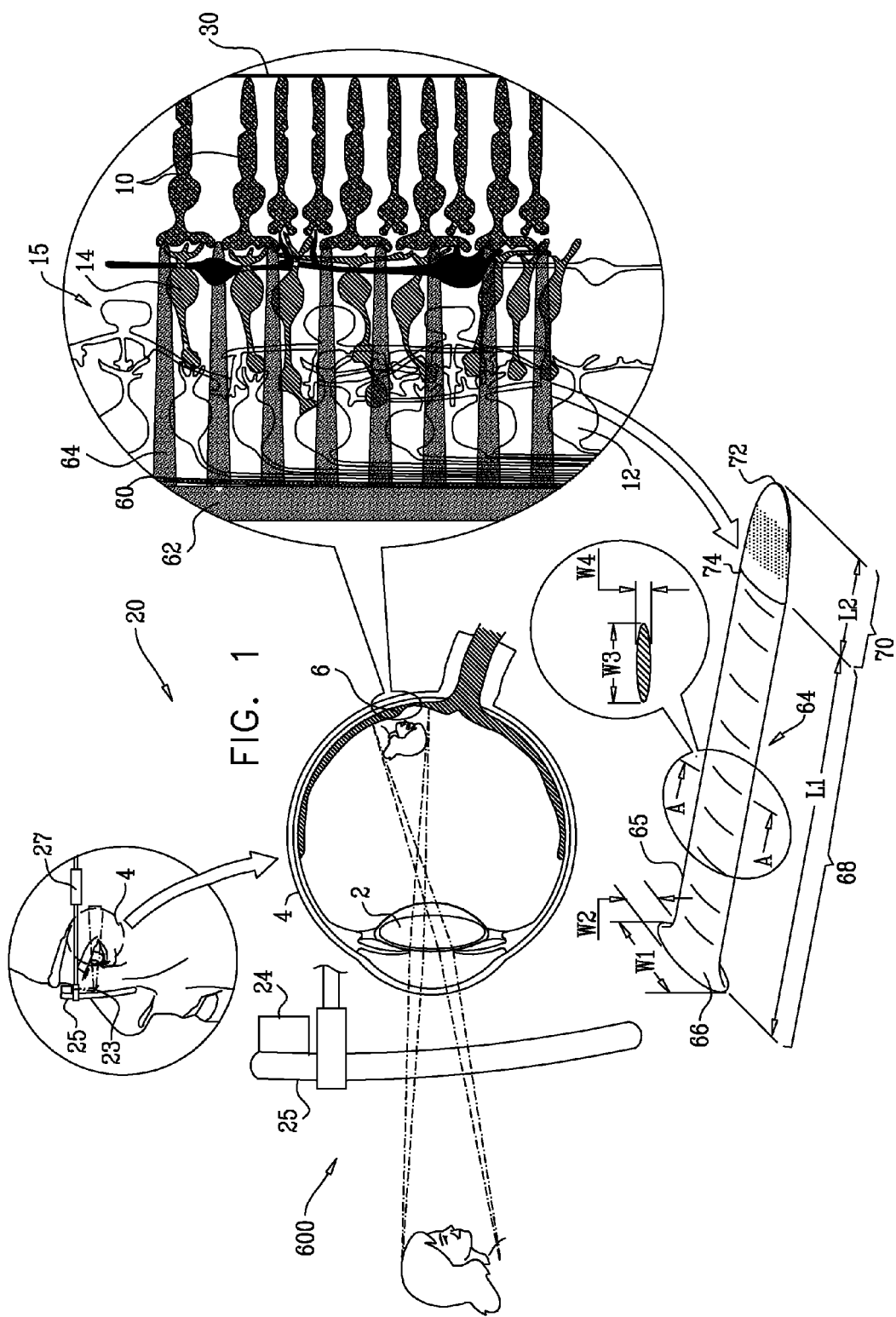
FIG. 1 shows a system for restoring at least partial vision in a subject in accordance with some applications of the present invention.

FIG. 1 shows a system 20 for restoring at least partial vision in a subject, a portion of which is implanted in an eye of the subject, in accordance with some applications of the present invention.

Vision is initiated when light reflecting from objects is focused by lens 2 of eye 4 onto the retina 6. FIG. 1 shows a cross section of a portion of a human retina. The retina is approximately 0.2-0.5 mm thick and lines the back of the eye. As shown, the retina consists of three layers of neurons: photoreceptor cells 10, ganglion cells 12 and many interneurons 15 packed into the central part of the section of the retina intervening between the photoreceptors and the ganglion cells. The ganglion cells, which transmit visual information to the brain, lie innermost (as used herein) in the retina, i.e., on the side of the retina closest to the lens and front of the eye. The photoreceptor cells (e.g., rods and cones), which capture light and convert light signals into neural signals, lie outermost in the retina. The central part of the section of retina located between the photoreceptors and the ganglion cells includes the inner nuclear layer (INL), which is made up of bipolar cells 14 and other cells. Interneurons 15, e.g., horizontal cells and amacrine cells, facilitate regulation of the neural signal from the photoreceptors and the bipolar cells.

Bipolar cells 14 typically transmit signals from photoreceptors 10 to ganglion cells 12. The rod and cone photoreceptors transfer a signal to the bipolar cells that lay adjacent to the photoreceptor layer. The bipolar cells then transmit the signal to the ganglion cells whose axons form the optic nerve. The bipolar cell 14 are generally located in a region of the retina that is approximately 130 um-200 um from the inner limiting membrane (ILM), which is the boundary between the vitreous humor in the posterior chamber and the retina itself.

As shown in FIG. 1, for some applications, an intraocular device 60 is implanted in an epi-retinal position, typically coupled to the ILM. As described in Zrenner, 2002, which is incorporated herein by reference, epi-retinal arrays are typically implanted onto the retinal surface that separates the retinal neural layer from the vitreous body of the eye's posterior chamber, such that the implant is typically located outside of the vitreous body, contacting the ILM. As appropriate, techniques described in one or more of these references may be adapted for use in implanting device 60.

For some applications, device 60 is implanted in a sub-retinal position (not shown). As described in Zrenner, 2002, which is incorporated herein by reference, sub-retinal arrays are typically implanted between the pigment epithelial layer 30 and the layer of the retina which contains photoreceptor cells 10.

As provided by some applications of the present invention, device 60 comprises a support substrate 62 and a plurality of electrodes 64 protruding from the support substrate. Support substrate 62 comprises components of an intraocular retinal prosthesis. For example, support substrate 62 may comprise an energy receiving layer, a photosensor layer and driving circuitry. The driving circuitry is powered by the energy receiving layer, which typically receives energy from an external device 600 comprising an external power source 24 (e.g., a laser coupled to the frame of a pair of eyeglasses 25, and/or a radiofrequency (RF) power source, and/or another electromagnetic power source). For some applications a partially-transparent (e.g., half-silvered) mirror 23 is coupled to eyeglasses 25, providing ophthalmoscope functionality to the external device.

It is to be noted that for some applications, techniques and apparatus described herein with reference to the external and intraocular devices may be performed with techniques and apparatus described in the following references, which are incorporated herein by reference: (a) U.S. patent application Ser. No. 12/368,150 to Gross, entitled, "Retinal Prosthesis," filed Feb. 9, 2009, published as US 2010/0204754, and issued as U.S. Pat. No. 8,150,526, (b) U.S. patent application Ser. No. 12/687,509 to Gefen, entitled "Penetrating electrodes for retinal stimulation, filed Jan. 14, 2010, published as US 2011/0172736, and issued as U.S. Pat. No. 8,718,784, and/or (c)

PCT/IL2010/000097 to Gross entitled "Retinal Prosthesis," filed Feb. 3, 2010, and published as WO 2010/089739.

The driving circuitry drives electrodes 64 to apply electrical charges to the retina, in response to sensing by the photosensor layer, in order to stimulate the retina 6. Accordingly, system 20 for restoring vision in a subject does not comprise an extraocular camera, and intraocular device 60 does not receive image data from outside the eye, but rather utilizes the intact optics and processing mechanisms of the eye 4.

Intraocular device 60 typically comprises approximately 500-6000, e.g., 1000-4000, typically 1600 electrodes 64. For some applications, the electrodes protrude perpendicularly at least 50 um from the support substrate.

Each electrode is typically 100-1000 um in length e.g., 300-600 um, for example, 400 um, in order to reach the outer plexiform layer (OPL), where connections between the bipolar cells and the adjacent photoreceptor cells occur. For some applications, each electrode comprises an electrically-insulated body portion 68 coupled to an electrically exposed tip portion 70. Insulated portion 68 of the electrode has a length L1 of between 100 um and 650 um, e.g., 150 um. Exposed tip 70 of electrode 64 typically has a length L2 of between 25 um and 100 um, e.g., 50 um. Typically, electrode 64 has an exposed area of 750 um2. The electrodes 64 protrude from support substrate 62, such that when device 60 is implanted in an eye of a subject, electrodes 64 penetrate tissue of retina 6 and exposed tip portions 70 are typically disposed in layer of bipolar cells 14. Other dimensions of the electrodes are described hereinbelow, with reference to FIGS. 2-3.

FIG. 1 shows a schematic illustration of electrode 64, in accordance with some applications of the present invention. As shown, the insulated portion 68 of electrode 64 includes an elliptical proximal base portion 66 and an elongated body portion 65 extending between the base portion and the exposed tip 70. Tip 70 typically comprises distal tip 72 and tip base 74. Base portion 66 typically has a major axis W1 of between 25 um and 200 um, e.g., 100 um, and a minor axis W2 that is typically 10-100 um, e.g., 50 um. Base portion 66 typically has a larger average diameter than body portion 65, contributing to the structural strength of electrode 64. Body portion 65 is typically generally elliptical, and has a major axis W3 of between 15 um and 60 um, e.g., 30 um, and a minor axis W4 between 5 um and 20 um, e.g., 10 um. Typically, electrodes 64 have a cross-section of 50-200 um2, 20 um from distal tip 72. For some applications electrodes 64 have a cross-section of at least 200 um2, 20 um from distal tip 72.

For some applications, each electrode 64 is typically 25-100 um in length e.g., 50 um, in order to penetrate the nerve fiber layer (NFL) and reach the layer of ganglion cells 12 (GCL). Contacting the ganglion cells by electrodes 64 typically enables the use of a reduced amount of power in order to stimulate the ganglion cells. Close proximity to ganglion cells 12 generally results in more focused stimulation that enables higher pixel density for a given amount of electrical charge.

Figure 2A:
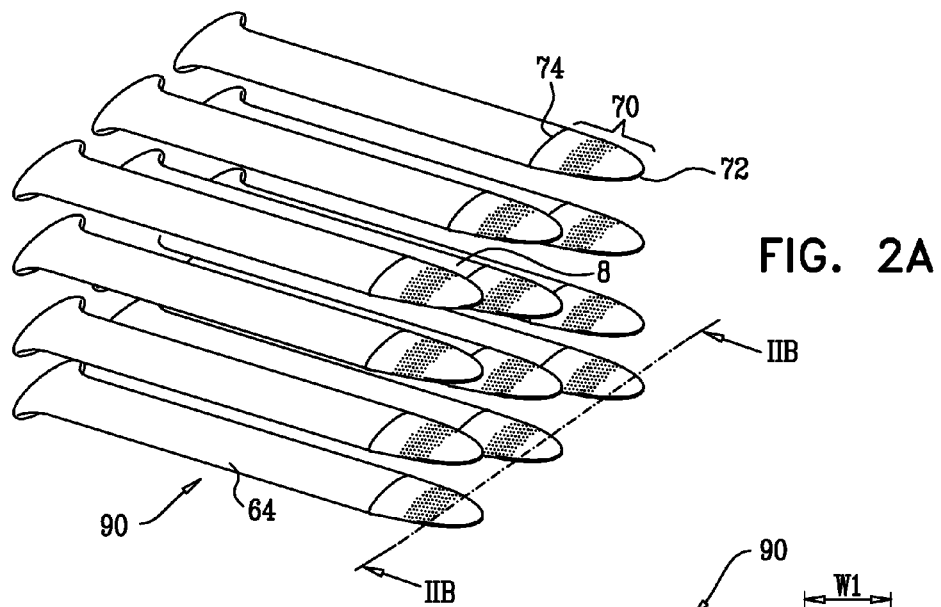
FIGS. 2A-B are schematic illustrations of an array of penetrating electrodes, in accordance with some applications of the present invention.

Reference is made to FIG. 2A, which is a schematic illustration of an array 90 of electrode 64, in accordance with some applications of the present invention. Tip portions 70 of electrodes 64 are typically shaped to define a plurality of perforations passing therethrough. In some applications, tips 70 are generally pointed, to facilitate tissue penetration. The perforated configuration of the tip allows for neuronal processes to intertwine with the electrode tips when electrodes 64 are disposed in retinal tissue of a subject. Increased and direct contact between the electrodes and the neuronal processes, improves the interaction between the neurons, e.g., bipolar cells, and the electrodes. Improved neuron/electrode interaction and coupling enhances stimulation of the neurons by the electrodes. Each tip 70 is typically shaped to define between 1 and 50 perforations (e.g., 1-10) passing therethrough. For some applications, the perforations of each electrode are located 5-20 um (e.g., 10 um) from distal tip 72 and 10-30 um from tip-base 74.

Typically, a spatial density of the perforations of each pointed tip is 0.001-0.02 perforations/um2, or 0.02 to 0.5 perforations/um2, e.g., 0.1 perforations/um2. For some applications, each perforation has a diameter of 1-10 um. The diameter of the perforations in electrode 64 allows axons of bipolar cells, which typically have an average diameter of 1 um, to penetrate and grow through the perforations.

As mentioned hereinabove, for some applications electrodes 64 are disposed in the layer of ganglion cells 12. In such applications, the axons of the ganglion cells grow through the perforations in electrode tips 70, increasing coupling between the neuronal processes and electrodes 64, and improving stimulation of the ganglion cell layer.

The average diameter of the perforations is typically smaller than the average diameter of a retinal glial cell, which is typically larger than 10 um, preventing glial cells from passing through the perforations in the electrode. Preventing glial cells from passing through the perforations reduces glial encapsulation of the electrodes, and prolongs electrode function.

The perforations are typically created by use of chemical treatments e.g., etching and/or a laser beam. For some applications, the same treatment is used to create the perforations and to increase surface roughness. For some applications, a surface of tip 70 of electrode 64 is coated with carbon nanotubes, attracting neuronal processes to the perforations in tip 70 and increasing adhesion of the neuronal processes to the perforations. Typically, the carbon nanotube coating within the perforation can withstand penetration of neuronal processes into the perforations.

Figure 2B:
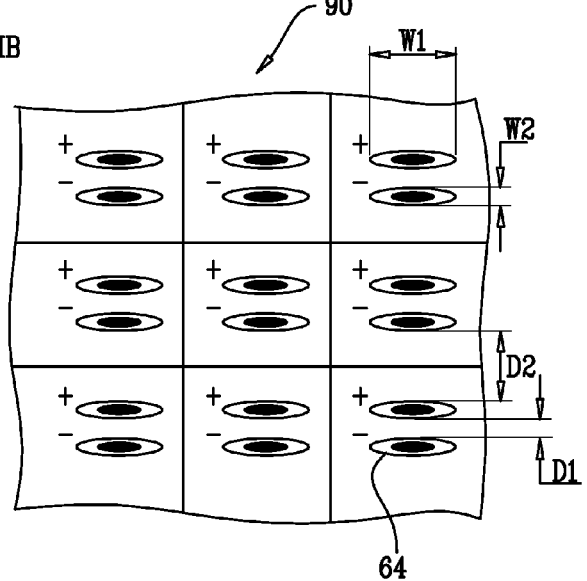

Reference is made to FIG. 2B, which is a schematic illustration of an end view of array 90 of electrodes 64, in accordance with some applications of the present invention. Device 60 typically comprises array 90 of electrodes 64 comprising at least 40 electrodes per mm2, e.g., between 100 and 400 electrodes per mm2. FIG. 2B shows array 90 divided into nine units by way of illustration and not limitation. For some applications, each unit is 100 um×100 um in size. Each unit typically comprises a pair of bipolar electrodes. For some applications, both bipolar electrodes (+ and −) in each unit protrude from array 90 and are configured to penetrate tissue of retina 6. One of these electrodes may be stimulating, and the other a return electrode, or else both may be stimulating. For some applications, the stimulating electrode is longer than the return electrode in each pair, and reaches the layer of bipolar cells, while the shorter return electrode only reaches the NFL layer. For other applications, one electrode (either the + or the −) protrudes from array 90 and is configured to penetrate tissue of retina 6, and the other electrode, of opposite polarity, is a surface electrode that is not configured to penetrate tissue of retina 6, but rather functions as a return electrode. The distance D1 between the pair of bipolar electrodes 64 in each unit is typically between 5 and 50 um, e.g., 10 um. The distance D2 between electrodes of adjacent units is typically between 25-100 um, e.g., 50 um. Generally, the distance D1 between a pair of electrodes in each unit is smaller than (e.g., less than half of) the distance D2 between electrodes of adjacent units.

Reference is made to FIGS. 1 and 2A-B. As shown in FIG. 2B, which is a Z view from the distal tip 72 of electrodes 64, the major axis W1 of base portion 66 of insulated portion 68 is typically 1.5-2.5 (e.g., 2) times larger than the minor axis W2 of body portion 65. Typically, major axis W1 is 25-200 um, e.g., 50-150 um (e.g., 100 um), and minor axis W2 is 10-100 um, e.g., 20-80 um (e.g., 50 um)

Reference is again made to FIGS. 1 and 2A-B. As mentioned hereinabove, for some applications, electrodes 64 comprise bipolar electrodes that are configured to penetrate retinal tissue of a subject. Penetrating bipolar electrodes, which are typically implanted such that both the stimulating and return electrodes are in close proximity to a neuronal retinal cell, require a smaller potential between the electrodes and enable reaching a higher potential drop across a given cell, resulting in enhanced stimulation of the cell. This is in contrast to many epi-retinal implants known in the art in which neuronal cells of the retina are stimulated by a surface electrode on the ILM layer.

For some applications, an array 90 of electrodes 64 is divided into subsets of electrodes. For such applications, a subset of three or more, e.g., 3-6, stimulating electrodes, by way of illustration and not limitation, surround and share a common return electrode 8. Each electrode in the subset receives a signal, through driving circuitry, from a discrete, respective, photosensor in support substrate 62, and in response, stimulates the retina of the subject. In such applications, the return electrode typically has a sufficiently large surface area in order to accommodate the electric charge returning from the subset of stimulating electrodes. Generally, such an arrangement of array of electrodes 64 enables the use of a reduced number of electrodes, since several stimulating electrodes share a common return electrode. For some applications, the stimulating electrodes are configured to drive electrical charges into the cells of retina non-simultaneously. Such staggering of the driving of each electrode in the subset reduces the amount of return electrical charge that is driven through the return electrode at a given time. For some applications, array 90 comprises at least 10 subsets of electrodes, e.g., 100-500 subsets. For some applications, array 90 comprises 500-1500 subsets of electrodes.

Reference is again made to FIGS. 2A-B. Electrodes 64 are typically fabricated by conventional fabrication processes known in the art. For some applications, following fabrication, electrodes 64 are assembled on array 90 by methods such as "pick and place." For other applications, other methods are used to fabricate array 90 of electrodes 64, e.g., three dimensional etching and/or MEMS Palladium etching technique. For some applications, techniques described in one or more of the following patents are practiced in combination with techniques and apparatus described herein: U.S. Pat. Nos. 7,096,568, 6,678,458, 6,923,669, 6,473,365, 6,762,116, 7,025,619, 7,081,630 and 6,677,225 which are incorporated herein by reference.

Figure 3:
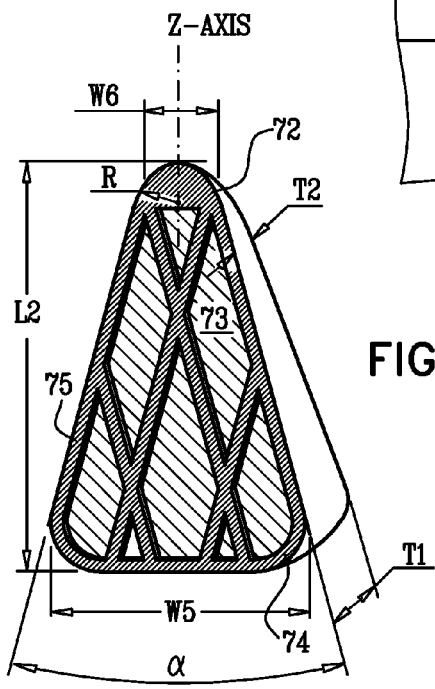
FIG. 3 is a schematic cross-sectional illustration of a pointed tip an of electrode, in accordance with some applications of the present invention.

Reference is now made to FIG. 3, which is a schematic cross-sectional illustration of a tip portion 70, in accordance with some applications of the present invention. Intraocular device 60 comprises electrodes which, for some applications, are shaped to define respective pointed tips configured for penetrating tissue of the subject. Each tip 70 is typically an electrically exposed tip, configured to directly drive electrical charge into the retinal tissue, e.g., bipolar cells, causing stimulation of the tissue and resulting in enhanced vision. Exposed tip 70 of the electrode typically has a length L2 of between 25 um and 100 um, e.g., 50 um. Typically, although each tip 70 is pointed when viewed from a distance, and thus functions as a pointed tip for purposes such as penetrating tissue, a close examination of the tip 70 reveals that it is shaped to have a radius of curvature R of 0.5-10 um, e.g., 2 um.

Tip 70 may be shaped to define a tip having an angle alpha of 30-60 degrees. As shown in FIG. 3, tip 70 comprises a tip-base portion 74 and a distal tip 72. Base portion 74 of tip 70, which is at a distal end of the electrode body portion, has a width W5 of between 15 um and 60 um, e.g., 30 um. Tip 70 typically decreases monotonically in width along its longitudinal axis from tip-base portion 74 to distal tip 72, until it reaches a width W6 of between 1 um and 20 um, e.g., 10 um, 4 um proximal from distal tip-end 72. For some applications, tip 70 is reduced in size after electrode shaping by techniques such as laser ablation.

As shown in FIG. 3, tip 70 typically decreases monotonically in thickness along its longitudinal axis from base portion 74 to distal tip 72. Base portion 74 of tip 70 has a thickness T1 of between 5 um and 20 um, e.g., 10 um. Distal tip 72 of tip 70 has a thickness T2 of between 0.5 um and 5 um, e.g., 2 um. The shape of the distal tip of tip 70, and a radius of curvature R of tip 70, typically reduces the extent to which tip 70 penetrates and/or ruptures cells with which it comes in contact. Typically, retinal neuronal cells range between 5 and 10 um. Radius of curvature R is typically 0.5 um-10 um, e.g., 2 um, roughly in the same magnitude as the cells. Generally, all edges of electrode tip 70 and electrode 64 have a radius of curvature that is greater than 0.1 um, e.g., greater than 0.5 um. Rounding of the edges is typically done to reduce concentration of charge at sharp edges. Surface treatments to increase roughness of a surface of tip 70, as described hereinbelow, are also used to smoothen and round edges of tip 70 and electrode 64.

Typically, tip 70 of electrode 64 is treated to increase surface roughness of tip 70. For some applications, an area 73 of tip 70 is treated to increase roughness, whereas another area 75 of tip 70 remains untreated in order to maintain structural strength of the tip.

Reference is made to FIGS. 2A-B and 3. As shown in FIG. 3, untreated areas 75 are maintained in order to strengthen tip 70 for withstanding compression forces applied during penetration of tip 70 into retinal tissue. Surface treatment of the tip in areas 73 typically affects an area of the tip that is as deep as 2 um from the surface. Increased surface roughness causes an increased surface area of the tip. The tip is treated to increase roughness such that 1 mm2 area has an equivalent surface area of between 10 mm2 and 1000 mm2, e.g., 100 mm2. Increased surface area generally reduces electrode impendence, thereby enhancing stimulation of retinal tissue by electrodes 64. Additionally, increased roughness generally reduces surface charge density and improves electrode capacitance, enabling an increase in the charge injection limit. Increased surface roughness to reduce charge density is typically achieved by techniques of nanofabrication and/or metal etching, as described in Liang et al., in an article entitled "Surface modification of cp-Ti using femtosecond laser micromachining and the deposition of Ca/P layer" Materials Letters Volume 62, Issue 23, 31 Aug. 2008, Pages 3783-3786, which is incorporated herein by reference.

For some applications, electrodes 64 are coated with carbon nanotubes. Typically, carbon nanotubes create a rough surface in electrode 64, including tip portion 70. Rough surfaces in general and carbon nanotube surfaces in particular have been shown to attract neurons and promote neuronal growth. As described in an article by Sorkin et al., entitled "Process entanglement as a neuronal anchorage mechanism to rough surfaces," Nanotechnology 20 (2009) 015101 (8 pp), which is incorporated herein by reference, neurons were found to bind and preferentially anchor to carbon nanotube rough surfaces. Thus, adhesion of retinal neurons, e.g., bipolar cells, to carbon nanotube electrodes provided by these applications of the present invention, promotes cell-electrode coupling and/or axon regeneration, leading to improved stimulation of the retina. For some applications, the carbon nanotube coating of electrode 64 is glued to the electrode surface and/or grown on a selected surface of the electrode by using doping techniques known in the art.

For some applications, a femtosecond laser is used to increase surface roughness of electrodes 64. Femtosecond laser treatment produces rough surface structures on titanium possibly for the use of implants and other biomedical applications treatments (Vorobyev et al., 2007 referenced above). As described in an article by Vorobyev et al., entitled "Femtosecond laser structuring of titanium implants," Applied Surface Science, Volume 253, Issue 17, 30 Jun. 2007, Pages 7272-7280, which is incorporated herein by reference, femtosecond laser treatment increases the roughness of a titanium substrate in the range of 1-15 um. Additionally, femtosecond laser treatment was shown to produce a variety of surface nanostructures, such as nanoprotrusions and nanopores on the titanium substrate. Liang et al., 2007, cited above, report good bioactivity of a pure titanium substrate that was treated with a femtosecond laser to increase roughness of its surface.

For some application, a blanket etch MEMS procedure is used to increase surface roughness of electrodes 64. For such applications, the entire electrode 64 is blanketed and tip 70 is etched to increase surface roughness and achieve a desired aspect ratio in a similar procedure to that described in U.S. Pat. No. 6,770,521 to Visokay.

Reference is made to FIGS. 4A-B, which are schematic illustration of intraocular device 60, in accordance with some applications of the present invention. Device 60 typically comprises an array 1090 of protruding electrodes 1064 configured to penetrate the retina of a subject. It is to be noted that techniques and apparatus described herein with reference to electrodes 64 and array 90 apply to electrodes 1064 and array 1090, and vice versa, except where otherwise indicated. For some applications, electrodes 1064 vary in length. Electrodes 61 are generally longer than electrodes 62, thereby facilitating direct stimulation of distinct areas of the retina, e.g., layer of the bipolar cells and/or the layer of ganglion cells. Other dimensions of the electrodes are described hereinbelow, with reference to FIG. 6.

Electrodes 1064 comprise any suitable material e.g., palladium and/or titanium, and/or silicon electrodes. For some applications, electrodes 1064 comprise a metal alloy and/or doped electrodes. Typically, a silicon wafer 1030 forms the base of array 1090 from which electrodes 1064 protrude. For some applications, wafer 1030 is selectively etched to a desired depth by using any suitable technique known in the art, e.g., techniques of Deep Reactive Ion Etching (DRIE). For some applications, following bonding of the silicon wafer, electrodes 1064 are etched by using any suitable technique known in the art, e.g., techniques of Deep Reactive Ion Etching (DRIE), to have desired dimensions and aspect ratios. For some applications, additional metals such as platinum, and/or palladium, are deposited on electrodes 1064 by using, for example, a shadow mask technique. An attaching titanium ring frame 1020 is typically electroplated with electrodes 1064 to form structure that can subsequently be welded to the metal ring case 2020 (shown in FIG. 5). The silicon wafer 1030 is typically biocompatible. Ring frame 1020 is typically bonded to silicon wafer 1030, by using, e.g., fusion bonding. Suitable fusion bonding techniques are described in an article by Jourdain et al., entitled, "Fabrication of piezoelectric thick-film bimorph micro-actuators from bulk ceramics using batch-scale methods," which is incorporated herein by reference. Wafer 1030 typically comprises through-wafer vias.

Typically, device 60 additionally comprises a CMOS chip 1040 including through-silicon vias. For some applications, solder bumps 1050 are deposited on an upper side of CMOS chip 1040, electrically connecting chip 1040 to silicon wafer 1030. Additionally, for some applications, device 60 comprises a layer 1060. Layer 1060 typically comprises additional elements of an intraocular retinal prosthesis, e.g., an energy receiving layer, a photosensor layer and driving circuitry that is powered by the energy receiving layer. The driving circuitry typically drives electrical charge into the retinal tissue from the rough tips 1070 of electrodes 1064, in response to sensing by the photosensor layer, in order to stimulate the retinal tissue. The electrical signal generated by layer 1060 is typically routed through silicon wafer 1030 to electrodes 1064, providing sealing on one side and electrical contact on the other.

For some applications, a back side of the titanium wafer is bound to a glass cap 80 which, as shown in FIG. 4B, encapsulates the entirety of intraocular device 60, excluding array 1090 of protruding electrodes 1064. For some applications, glass cap 80 comprises two distinct glass pieces, one of which is shaped to define a hole. The glass pieces are typically bonded to each other by anodic bonding, forming a single glass cap 80. Bonding of titanium frame 1020 to glass cap 80 is optionally done using thermal compression bonding. This low temperature bonding step generally does not affect circuitry of intraocular device 60. Glass cap 80 generally reduces exposure of human tissue to any toxic materials, e.g., contaminated silicon, which may exist in intraocular device 60. Typically, laser welding is used to close the glass encapsulation.

Reference is made to FIG. 5, which is a schematic illustration of intraocular device 60, in accordance with some applications of the present invention. As described hereinabove, intraocular device 60 typically comprises array 1090 of electrodes 1064, which are configured to penetrate retinal tissue of a subject. For some applications, electrodes 1064 comprise long electrodes 61 and short electrodes 62. Array 1090 is typically bonded to silicon wafer 1030 which is coupled to CMOS chip 1040 via solder bumps 1050. As shown in FIG. 5, for some applications, intraocular device 60 comprises a metal ring 2020 which encapsulates the entirety of intraocular device 60, excluding array 1090 of protruding electrodes 1064. For some applications, metal ring 2020 functions as DC grounding for electrodes 1064. Additionally, in a case in which an electrode is not active, it may be held to ground by activating a switch that locks the electrode to metal ring 2020, such that the electrode stays at ground.

Reference is now made to FIGS. 1 and 5. As described hereinabove with reference to FIG. 1, each electrode in intraocular device 60 comprises an electrically-insulated body portion coupled to an electrically exposed distal tip. FIG. 5 shows an exploded view of electrodes 1064 showing body portion 1068 of electrodes 1064 coated with a polyimide insulating coating 82. Tip 1070 of electrode 1064 remains electrically exposed, i.e., not coated with a polyimide coating, to enable an electrical connection between the tip and the bipolar layer (or other portions of the retina). As described hereinabove, in some applications, tip 1070 physically contacts the layer of bipolar cells 14 when intraocular device 60 is implanted in the eye of a subject. For some applications, the entire electrode is fabricated to include a polyimide coating, followed by for example, an etching process to selectively remove the polyimide coating from electrode tip 1070. Alternatively, the polyimide coating is removed from the tip 70 by laser ablation. Seo et al., in an article entitled "Biocompatibility of polyimide microelectrode array for retinal stimulation," Materials Science and Engineering: C, Volume 24, Number 1, 5 Jan. 2004, pp. 185-189(5), which is incorporated herein by reference, report that polyimide is a suitable material for a retinal prosthesis.

As described hereinabove with reference to FIG. 3, the electrically exposed tips of the electrodes are treated to increase surface roughness. Accordingly, FIG. 5 shows tip 1070 having a rough surface to increase neuronal cell adhesion to tip 1070, thus increasing tissue stimulation by electrodes 1064. Typically, tip 1070 is configured to penetrate retinal tissue of a subject.

Typically, intraocular device 60 is configured to match the natural curvature of the retina to facilitate implantation and anchoring of intraocular device 60 to the retina. Accordingly, electrodes 1064 typically vary in length, and as indicated by FIGS. 4A-B and 5, for some applications, tips 1070 of electrodes 1064 together define a convex curved surface having a radius of curvature that is 6-15 mm.

Figure 6:
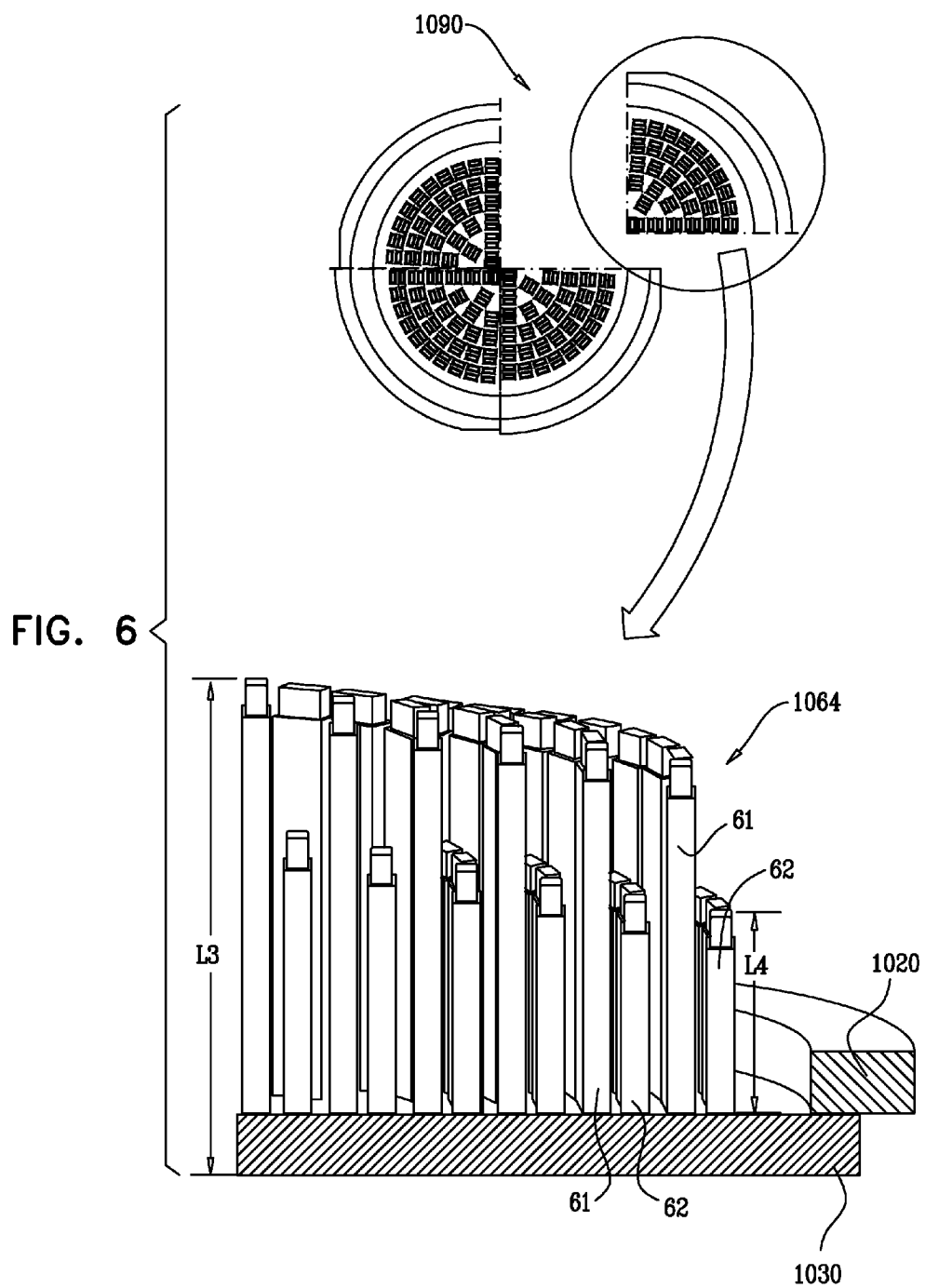
FIG. 6 is a schematic illustration of an array of penetrating electrodes, in accordance with some applications of the present invention.

Reference is made to FIG. 6 which is a schematic illustration of a section of array 1090 of electrodes 1064, in accordance with some applications of the present invention. As shown, array 1090 typically comprises electrodes 1064 of varying heights. For some applications, electrodes 1064 are arranged in concentric circles on wafer 1030. The circles of electrodes 1064 typically alternate between long electrodes 61 and short electrodes 62, such that electrodes 1064 are typically arranged in pairs of bipolar electrodes. Each pair of electrodes typically comprises a single long electrode 61 and a single short electrode 62.

Intraocular device 60 and electrodes 1064 are typically configured to match the natural curvature of a human organ and/or tissue in which it is implanted, e.g., the retina. As shown in FIG. 6, for some applications, electrodes 1064 vary in length. Electrodes 61 are generally longer than the electrodes 62, thereby facilitating direct stimulation of distinct areas of the retina, e.g., layer of bipolar cells and/or the layer of ganglion cells. For some applications, long electrodes 61 have a length L3 of 200-800 um, e.g., 300-500. Short electrodes 62 typically have a length L4 of 100-550 um, e.g., 150-350. Typically long electrodes 61 are 50-150 um longer than the adjacent short electrodes 62. For some applications, both long electrodes 61 and short electrodes 62 function as stimulating electrodes. For other applications, long electrodes 61 function as stimulating electrodes and short electrodes 62 function as return electrodes. For some applications, return electrodes 62 are less than 10 um in length, and may even comprise surface electrodes. In this case, L4 is less than 5 um in length.

Figure 7:
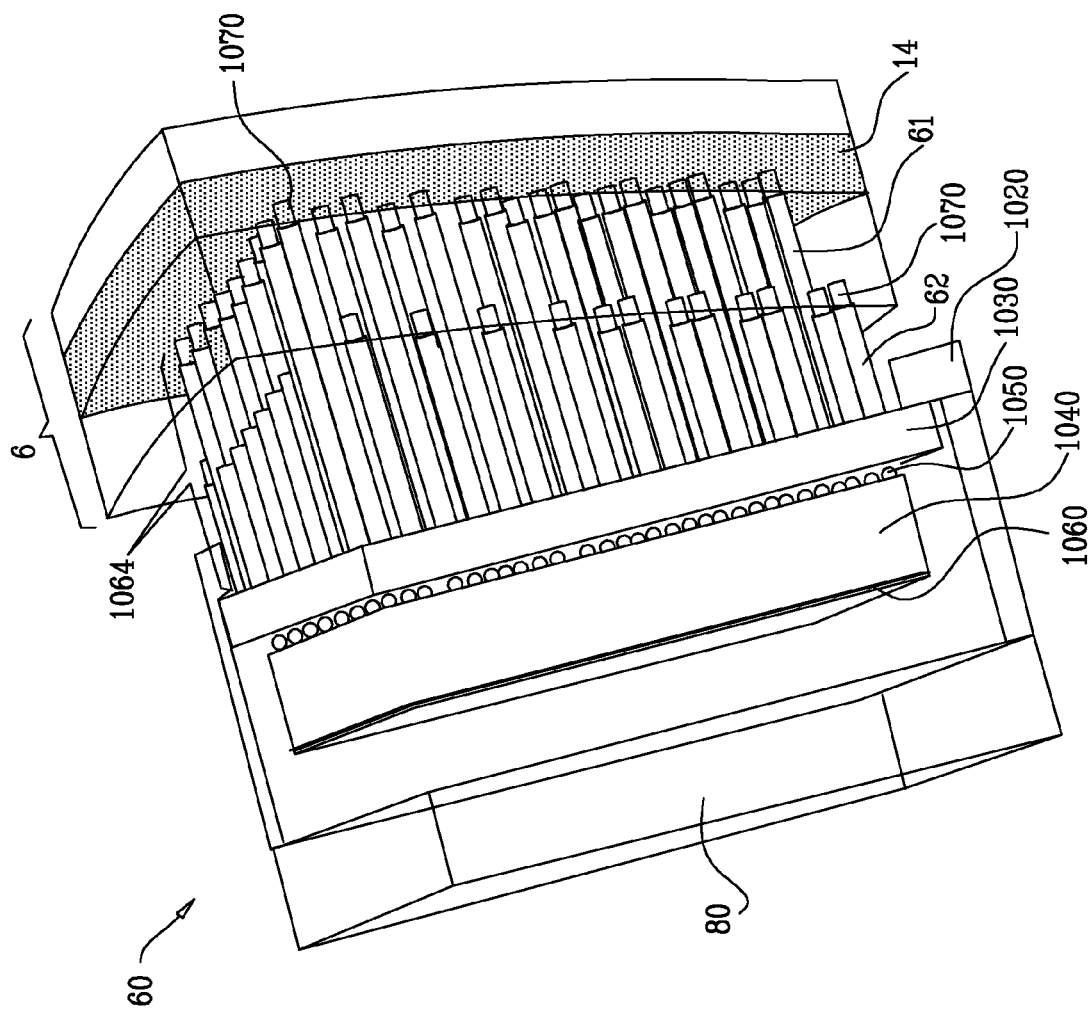
FIG. 7 is a schematic illustration of an intraocular device penetrating retinal tissue, in accordance with some applications of the present invention.

Reference is made to FIG. 7, which is a schematic illustration of device 60 disposed in retina 6, in accordance with some applications of the present invention. FIG. 7 shows components of device 60 (silicon wafer 1030, attaching ring frame 1020, CMOS chip 1040, solder bumps 1050 and layer 1060) in glass encapsulation 80. Electrodes 1064 are shown penetrating retina 6. For some applications, and as described hereinabove with reference to FIG. 6, electrodes 1064 of intraocular device 60 are arranged in pairs of bipolar electrodes. For some applications, both bipolar electrodes (+ and −) of each pair protrude from intraocular device 60, and are configured to penetrate tissue of retina 6. For some applications, the electrodes in each pair are of varying lengths, such that one electrode (either the + or the −) is longer than the second electrode. Typically, the longer electrode 61 (e.g., 200-800 um in length) is configured to protrude from intraocular device 60 and penetrate retinal tissue in order to contact and stimulate the bipolar cell layer. The shorter electrode 62 (e.g., 100-550 um in length) is typically configured to protrude from intraocular device 60 in order to contact and stimulate epi-retinal tissue, e.g., the NFL layer. Additionally or alternatively, short electrode 62 is configured to penetrate and stimulate retinal ganglion cells. For some applications, long electrodes 61 function as stimulating electrodes, e.g., to stimulate the bipolar cells and short electrodes 62 function as return electrodes.

For other applications, one electrode (either the + or the −) protrudes from intraocular device 60 and is configured to penetrate tissue of retina 6, and the other electrode, of opposite polarity, is a surface electrode that is not configured to penetrate tissue of retina 6, but rather functions as a return electrode (application not shown). Typically, intraocular device 60 comprises at least 100 short or surface electrodes, and at least 400 long electrodes.

For some applications, electrodes 1064 comprise hook electrodes configured to anchor to retinal tissue of a subject, increasing coupling between the target cells and the electrode.

Reference is made to FIGS. 1-7. For some applications, intraocular device 60, including substrate 62, is flexible and can be adjusted to match the natural curvature of the retina during implantation. Intraocular device 60 may be adjusted to match the retina of a subject by standard fitting and/or can be tailor made according to OCT imaging of the retina. Once adjusted to match the natural curvature of the retina, intraocular device 60 is typically glued and/or stitched in place. For other applications, intraocular device 60 is generally rigid, and electrodes of varying heights and, optionally, shapes enable proper attachment of the intraocular device to the curved structure of the retina.

Reference is again made to FIGS. 1-7. It is to be noted that a plurality of implantable devices 60 may be implanted in discrete locations in tissue of retina 6, either arranged in an array, or, for example, pseudo-randomly. Typically, intraocular device 60 is wireless and does not comprise bulky components, facilitating implantation of several implants 60 in retina 6 of the subject.

It is to be noted that a system comprising penetrating electrodes with rough and/or perforated tips as described hereinabove with reference to FIGS. 1-7, may be implanted in any other organ (e.g., brain, nose, ears and/or tongue), and used in any other neurological application (e.g., cortex stimulation). Implantation of penetrating electrodes as described hereinabove in, for example, brain tissue of a subject typically reduces the amount of power required to stimulate the tissue. Additionally or alternatively, implantation of such electrodes facilitates specific sensing and enhances specific stimulation of a target neuron in the tissue by directly contacting selective areas with the electrodes.

For some applications, a system comprising penetrating electrodes as described hereinabove may be used to stimulate organs such as the liver or the pancreas. Implanting an array of such electrodes in, for example, selected areas of pancreatic tissue (e.g., insulin-secreting areas) enables specific and more effective stimulation of these areas.

Reference is again made to FIG. 4. For some applications, layer 1060 is a multilayer array comprising an energy receiving layer, a photosensors layer and driving circuitry that is powered by the energy receiving layer. The driving circuitry typically drives current into the stimulating electrodes 1064, in response to sensing of ambient light by the photosensor layer, in order to stimulate the retinal tissue. Alternatively, layer 1060 comprises a single layer array configured both for energy receiving and photosensing. For some applications a portion of the single array is configured for energy reception and a separate portion of the array is configured for photosensing. Alternatively, for applications in which a single layer is configured both for energy receiving and photosensing, the entire layer is configured, during alternating time periods, to (a) receive energy from power source 24 (shown in FIG. 1) to power the driving circuitry, and (b) sense ambient light and responsively transmit a signal to the driving circuitry.

Reference is made to FIG. 8, which is a block diagram of the transmission of energy, information, and instructions, in system 20, in accordance with some applications of the invention. External device 600 is located outside of a body of a subject and comprises power source 24, which emits energy to power components of intraocular device 60. The energy which is transmitted to device 60 is received by energy receiver 32. Energy receiver 32 typically comprises a voltage regulator 29 configured to maintain a constant voltage level to power the components of device 60. Intraocular device 60 further comprises photosensors 34 configured to detect photons 33 and generate a photosensor signal responsively to the photons. It is noted that although photosensors 34 are generally shown and described herein as being positioned in intraocular device 60, the scope of the present invention includes coupling photosensors 34 to external device 600 (application not shown). For some applications, a single light receiving element indicated by box 210 functions, during alternating time periods, as an energy receiver 32 and photosensors 34. The photosensor signal is transmitted to driving circuitry 36, which drives the electrodes 1064 to apply electrical charges to cells of retina 6. As shown, system 20 typically comprises a control unit 200 configured to regulate operating parameters of intraocular device 60. For example, the control unit may regulate operation of photosensors 34.

Typically, photosensors 34 are arranged as an array of photosensors 34. In some configurations of device 60, each photosensor in the array of photosensors corresponds to a stimulating electrode in the array of electrodes 1064. For some applications, each photosensor functions independently, i.e., each photosensor receives photons 33 and in response sends signals to driving circuitry 36, whereupon the driving circuitry drives the corresponding electrode to apply electrical charge to the retina 6. Thus, intraocular device 60 comprises an array of photosensor units, each photosensor unit comprising a photosensor and a corresponding electrode. Accordingly, the degree of retinal stimulation applied by each photosensor unit in the intraocular device is dictated by the light received by that unit. For some applications, each photosensor unit translates the level of light received by that unit into a train of stimulation pulses that is applied to the retina by the electrode. Additionally, such conversion of intensity of received light to frequency of stimulation can include a log transformation, such that for example: x photons received by the photosensor unit translate into one stimulation pulse applied by the electrode, while 10× photons correspond to only 2 stimulation pulses applied by the electrode.

Although functioning independently from one another, for some applications, a central control unit 200 regulates the function of each photosensor and corresponding electrode unit. Additionally or alternatively, each photosensor unit is configured to communicate with other units located in close proximity, and to modulate the electrical charge it drives into the retina in response to the functioning of neighboring units. Regulation of the electrical charge applied by each unit in the array of photosensors 34 with respect to other units in the array facilitates regulation of diverse features of visual perception. Varying the electrical charges applied to retinal neurons allows improved processing of the electrical charge by the retinal neurons e.g., bipolar cells.

For some applications, processing is performed by control unit 200. In some configurations of intraocular device 60, there is a larger number of photosensors than stimulating electrodes. For example, processing by control unit 200 can include disabling a bad pixel, improving focus of an image, sharpening, level adjustment, edge enhancement, and motion detection. Typically, this is performed using the data provided by the significantly larger number of photosensors than stimulating electrodes. Thus, edge detection and enhancement (or other image processing techniques) are performed using the hundreds of data points (or more), which are available to the control unit after having been sampled by the individual photosensors. This processing is used to allow the smaller number of stimulating electrodes to apply a more meaningful form of retinal stimulation, which reflects the output of the image processing (e.g., by showing an enhanced edge, emphasizing motion, or sharpening individual elements of an image). The scope of the present invention includes performing any of the image processing techniques described herein, even if the number of photosensors is not smaller than the number of stimulating electrodes. For some applications, a standard process is utilized in order to, e.g., enhance sensitivity by summation, edge detection for a clearer image, noise reduction in time and space, and/or adaptive dynamic range. Alternatively, the control unit facilitates processing, such as edge enhancement, by horizontal and/or amacrine cells of the retina, by providing a simpler image than that imaged by the photosensors. This simpler image is more easily processed by the retina neuron network.

For some applications, intraocular device 60 comprises protruding electrodes which are sufficient in length to contact bipolar cells 14 (shown in FIG. 1), thereby directly driving electrical charges into the bipolar cells. Thus, the electrical charge from the electrodes is directly driven into the bipolar cells, which transmit the viewed image via the ganglion cells and the optic nerve to the brain. Additionally, other retinal neurons, e.g., horizontal cells and/or amacrine cells, perform image processing to enhance and improve the received image. Examples of such processing include: focusing, edge detection, light adjustment, averaging, and motion detection. By directly contacting the layer of bipolar cells, device 60 mimics the natural transferring of a signal from native photoreceptor cells directly to the bipolar cells, for processing by the bipolar cells. The photoreceptor nerve cells are typically connected by synapses to bipolar nerve cells, which are then connected to ganglion nerve cells 12. The ganglion nerve cells connect to the optic nerve fibers, which carry the information generated in the retina to the brain.

For some applications, device 60 may comprise protruding electrodes that are shorter in length (e.g., 50-200 um, e.g., 100-150 um) and configured to directly contact the layer of ganglion cells 12 (shown in FIG. 7). For some applications, control unit 200 is configured to perform processing of the signals from the photosensors, and directly apply the pre-processed electrical charges via the electrodes to the ganglion cells, e.g., as described hereinabove with respect to improving edge detection or other image processing techniques.

Reference is again made to FIG. 8. For some applications, central control unit 200 regulates the function of some or all photosensors 34 and their corresponding electrode(s) 1064, e.g., by controlling the duration of a sensing period of each photosensor. Typically, the amount of ambient light that lands on the array of photosensors is used by the central control unit to determine the duration of a sensing period of each photosensor, i.e., the amount of time in which the photosensor receives photons before the driving circuitry drives the corresponding electrode to drive electrical charge into retinal tissue (e.g., 0.1 ms-30 ms). Thus, for example, the sensitivity of each photosensor may be increased over the course of several seconds, if the subject enters a dark room.

Additionally or alternatively, central control unit 200 sets the duration of an energy receiving period, i.e., the amount of time in which energy receiver 32 receives energy from external power source 24 before that energy is passed to driving circuitry 36 to drive the electrodes to drive electrical charges into retinal tissue (e.g., 1-10 ms, or 10-100 ms). For example, control unit 200 may increase the duration of an energy receiving period to supply device 60 with a sufficient amount of energy, e.g., if the subject increases the intensity such that a larger amount of electrical charge is applied through the electrodes, resulting in device 60 requiring an increased amount of energy. Further additionally or alternatively, central control unit 200 regulates the stimulation timing.

Reference is still made to FIG. 8. For some applications, in addition to supplying power to device 60, the energy emitted by power source 24 is used to regulate operation of intraocular device 60. This regulation may be in real-time, e.g., where the duration of each laser pulse corresponds to the duration of stimulation applied by an electrode to the retina. Alternatively, this regulation is not in real-time, e.g., conveying a digital message to the controller, which, in turn, modulates the stimulation signal (for example to increase exposure time). In some applications, external device 600 comprises a control element 27 (e.g., a dial, switch, or button) coupled to eyeglasses 25 (shown in FIG. 1), allowing the subject to interactively control the intensity of the electrical charge applied to retina 6 and/or the sensitivity of photosensors 34 to received light, and/or another system parameter. Typically, the intensity of the electrical charge applied to the retina by the electrodes is determined by driving circuitry 36, which drives electrodes 1064 to apply the electrical charge in pulses of electrical charge. The driving circuitry is configured to alter the intensity of electrical charge applied to the retina by regulating a stimulation parameter such as a number of the pulses, a frequency of the pulses, duration of each pulse, or a pulse repetition interval of the pulses. Additionally or alternatively, the driving circuitry is configured to control amplitude of the electrical charges applied by the electrodes. Control unit 200 is configured to regulate the function of the driving circuitry to adjust the intensity of the electrical charge based on the subject's input. Additionally, for some applications, the sensitivity of photosensors 34 to received light is determined by the duration of a sensing period of photosensors 34. Control unit 200 is configured to increase or decrease sensitivity of device 60 in response to the subject's input, e.g., by regulating the duration of a sensing period.

For example, if the subject determines that the overall stimulation being applied by device 60 to the retina is too strong, then he can adjust a setting on the control element to reduce the stimulation strength. Similarly, if he senses that his entire visual field is over-stimulated, indicating that the sensitivity of photosensors 34 is too high (e.g., resulting in the entire array of electrodes activating the retina at high intensity), then he can adjust another setting on the control element to reduce the sensitivity. In response to the subject's input, the energy emitted by the power source is modulated to regulate operating parameters of device 60, e.g., to increase or decrease intensity and/or sensitivity. An example of a suitable modulation protocol includes a first train of six short pulses from power source 24, indicating that stimulation intensity is going to be changed, followed by a train of between one and ten longer pulses indicating a subject-selected desired level of stimulation intensity. To change sensitivity, a first train of six long pulses is emitted from power source 24, followed by a train of between one and ten longer pulses indicating a subject-selected desired level of sensitivity. A person of ordinary skill in the art will appreciate that other encoding protocols may be used, as well.

For some applications, intraocular device 60 (e.g., the control unit of device 60) is configured to regulate the operation parameter of device 60 based on amplitude modulation of the light emitted by the power source 24 and received by energy receiver 32. Typically, the amplitude modulation varies between a minimum signal level and a maximum signal level. For some applications the minimum signal is at least 20% of the maximum signal (e.g., at least 50% of the maximum level). Typically the light emitted by power source 24 is modulated such that a carrier frequency of the modulated light is 10-100 kHz and a pulse width of pulses of the modulated light is 1-10 usec. For some applications, frequency modulation of the emitted light is used instead of or in addition to amplitude modulation.

In some applications, the minimum signal level is at least 20% (e.g., at least 50%) of a summed strength of (a) light received by intraocular device 60 from power source 24 and (b) ambient light received by the intraocular device. For some applications, external device 600 comprises a sensor configured to sense a level of ambient light and change the modulation of the light emitted by the power source 24 accordingly. For some applications, control element 27 coupled to eyeglasses 25 (shown in FIG. 1), comprises this sensor, e.g., a photodiode, configured to sense the level of the ambient light. For some applications, intraocular device 60 comprises the sensor that senses the level of ambient light.

Alternatively or additionally, a filter, e.g., a narrow band filter, is associated with energy receiver 32 and is configured to substantially prevent the ambient light from reaching the energy receiver or being sensed by the receiver.

Typically, central control unit 200 receives modulated energy from energy receiver 32, and demodulates the energy to regulate operation of device 60 accordingly. For example, based on the subject's input, the energy emitted by power source 24 is modulated to signal to device 60 to decrease or increase sensitivity of photosensors 34. (For example, the modulation may include changes in pulse timing of pulses emitted by power source 24.) Control unit 200 is configured to demodulate the energy received by energy receiver 32 and, for example, accordingly determine the duration of a sensing period of the photosensors, i.e., the amount of time in which the photosensors receive photons before the driving circuitry drives the corresponding electrode to drive electrical charge into retinal tissue (e.g., 0.1 ms-5 ms, or 5 ms-100 ms). This thereby increases or decreases the sensitivity of the photosensors according to the subject's input. Additionally or alternatively, control unit 200 is configured to demodulate the energy received by energy receiver 32 and accordingly regulate the driving circuitry to alter the intensity of electrical charge applied to the retina by altering a stimulation parameter such as a number of the pulses, a frequency of the pulses, duration of each pulse, and a pulse repetition interval of the pulses.

Alternatively, the function of elements and/or arrays and/or sub-arrays of device 60 are controlled by several distributed control units.

For example, for some applications, each photosensor and corresponding electrode unit is controlled by an individual control unit which regulates system parameters, such as parameters of the photosensor. In an application, the sensitivity of the photosensors is regulated, for example, by setting the duration of a sensing period of each photosensor (i.e., the amount of time in which the photosensor receives photons before the driving circuitry drives the corresponding electrode to drive electrical charge into retinal tissue). For other applications, separate control units regulate the function of each subset of electrodes and corresponding photosensors.

Reference is made to FIGS. 1-8. For some applications, device 60 is configured to enable night vision (typically in addition to regular vision when there is sufficient light). Typically, photosensors 34 are sensitive to visible light and are configured to receive photons from ambient light and generate a signal in response thereto. For some applications, and in particular for conditions lacking ambient visible light, device 60 additionally comprises uncooled infrared (IR) detectors which receive incident IR radiation and produce an output signal depending on the amount of IR radiation landing on the detector. The uncooled IR detectors convert the incident IR radiation into an electrical current in device 60 which is conveyed to the driving circuitry, which in turn drives the electrodes to apply electrical charges to the retina, causing image formation.

Reference is again made to FIGS. 1-8. During implantation, device 60 is typically mechanically attached to the retina of a subject and/or glued into place.

Reference is still made to FIGS. 1-8. For some applications, electrodes 1064 are arranged in several subsets of electrodes. For some applications, device 60 comprises 10-2500 subsets, e.g., 100-500 subsets of electrodes. For some applications, array 1090 comprises 500-1500 subsets of electrodes. For some applications, each subset of electrodes comprises three or more electrodes. For some applications, an electrode in at least one of the subsets is within 300 um or 500 um of another electrode in the subset.

Typically each subset of electrodes shares a common power supply, e.g., a common capacitor, which provides current (typically non-simultaneously) to all of the electrodes in a respective subset. In such applications, the capacitor in each subset is sufficiently large (e.g., 0.01-0.1 nf, or 0.1 nf-1 nf) to allow charging to less than 50% of full-charge of the capacitor during each charging of the capacitor. Using a large capacitor generally enhances the efficiency of intraocular device 60, since it allows for the capacitor to quickly recharge once it has provided currents to the electrodes. In contrast, using a single small capacitor in order to drive a single electrode typically requires a longer recharging period and is therefore less efficient. However, it is generally not possible to have one large capacitor per electrode, in an array of 100-1000 electrodes. As provided by some applications of the present invention, an array of several subsets of electrodes, in which each subset is driven by a respective common large capacitor, allows for the use of a reduced number of large capacitors, thus allowing the use of a large capacitor to drive a plurality of electrodes and thereby improving efficiency of the device.

For some applications, electrodes 1064 are arranged in subsets of stimulating electrodes which surround and share a common return electrode (as described hereinabove). At least some of the stimulating electrodes 1064 in each subset are configured to drive electrical charges into the neurons of the retina in non-simultaneous time periods. Consequently, for such applications, the common return electrode receives electrical charges from at least some of the stimulating electrodes in the subset non-simultaneously. Such staggering of the driving of each electrode and of the returning current generally reduces interference and neuron load. Such staggering also reduces tissue damage and/or prolongs the lifetime of the return electrode. Additionally, for applications in which the electrodes are arranged in subsets of electrodes, staggering of the driving of each electrode generally reduces the charge density per subset. Additionally or alternatively, staggering of the driving of each electrode generally reduces interference between adjacent neuron fibers, typically leading to improved sensation of vision.

For some applications, no dedicated return electrode is provided, but instead while one electrode in a subset drives electrical charges into the retina, some or all of the remaining electrodes in the subset act, collectively, as a return electrode.

Typically, application of electrical charges to the cells may be programmed such that generation of sub-harmonics and/or beat frequencies, and/or artificial frequencies and/or sensations of a flicker are reduced. For example intraocular device 60 may be configured to apply electrical charge through electrodes 1064 in a subset using changing sequences. For example, apparatus 60 may be configured to apply electrical charge through four electrodes in a subset using the sequence 1-2-3-4, followed by applying the electrical charge in a different sequence (3-1-2-4), by way of illustration and not limitation. Alternatively, the electrical charge is applied using time-based jittering of at least some of the electrical charge applications, to reduce the generation of sub-harmonics and/or beat frequencies, and/or artificial frequencies and/or sensations of a flicker. For example, instead of applying electrical charge pulses separated by a standard time gap, the time gap can be "jittered" by introducing a time variation in the frequency of these successive electrical charge pulses. Alternatively or additionally, other signal parameters may be jittered, such as pulse duration and amplitude. For some applications, a fuzzy logic, multi-value, concept is applied. For example, instead of having a single fixed parameter for power amplitude or jitter, the system has a range of each parameter and it will scan through this range in a regular or pseudorandom procedure. (In biological systems, the exact parameter that will produce an optimal response at any time is changing, but the range of the parameter is generally known.)

For some applications, system 20 is configured to restore at least some color vision in a subject suffering from damaged retinal photoreceptor cells, e.g., cones, by stimulating intact portions of the retina, e.g., the bipolar cells. Most cones lie in the fovea, which defines the center of the retina. Humans normally have three types of cones responding to different wavelengths. A different signal is applied by the different cone types, allowing perception of different colors. A typical cone cell forms a synapse with a neuron such as the bipolar cell. Intraocular device 60 is configured to drive the electrodes to directly stimulate different bipolar cells resulting in perception of different colors. Additionally or alternatively, the electrical charge driven by the electrodes into the retina is modulated such that different stimulation patterns are applied to the retina resulting in the perception of color (e.g., red, green and/or blue). Intraocular device 60 can then be calibrated based on the subject's input as to which stimulation pattern (typically based on varying pulse parameters) creates an optimal perception of color.

Additionally, photosensors 34 are color sensitive and configured to distinguish between certain colors (e.g., red, green and/or blue). Accordingly, electrodes 1064 are typically designated red, green and/or blue (by way of illustration and not limitation), corresponding to the colors sensed by photosensors 34. According to the sensing of different colors, the driving circuitry in intraocular device 60 drives electrical charges through the corresponding electrodes, resulting in the sensation of different colors (typically after an acclimation and/or training period).

Reference is still made to FIG. 8. For some applications, energy receiver 32 and voltage regulator 29 are isolated from photosensors 34, to reduce noise levels in intraocular device 60. Photosensors 34 are typically highly sensitive to energy levels of less than 1 pW, and are as a result susceptible to noise. Electrical stimulation by contrast creates relatively high power (0.1-1 uW) electrical signals, for neuron activation. Accordingly, noise generated by the high power signal is typically filtered from entering into the photosensing circuitry. Such filtering is typically implemented in the VLSI electrical design. Additionally, voltage regulator 29 is a main connection between the two circuits and to reduce noise transfer it is typically divided into two different circuits.

For some applications, power source 24 of the external device comprises an RF emitting power source. For such applications in which the power source comprises an RF emitting power source, an intraocular lens (IOL) is implanted in the eye of the subject, replacing the native lens. Typically, an RF receiving coil configured to receive RF energy emitted from the power source is incorporated into the IOL (configuration not shown). Incorporation of the RF receiving coil in the IOL, instead of implanting such a coil in a small epi-retinal space, generally enables the use of a large diameter RF receiving coil (e.g., 8-14 mm in diameter). Additionally, an RF receiving coil which is located in the IOL is in relative close proximity to the RF power source, enabling the use of a reduced amount of energy. Typically, the macula of the retina is spaced about 4-5 cm from eyeglasses 25 (eyeglasses 25 are shown in FIG. 1), which are coupled to an RF energy source. Thus the IOL with the RF receiving coil is positioned approximately 1.5-2 cm from the RF energy source. This enables higher RF efficiency than if an RF receiving coil were implanted in the retina. An intraocular unit comprising photosensors, driving circuitry and stimulating electrodes is typically implanted in either an epi-retinal or a sub-retinal location and configured to receive the energy from the RF receiving coil. For some applications, a wire transferring energy from the RF receiving coil to the intraocular unit extends between the RF receiving coil in the IOL and the intraocular unit.

Figure 9A:
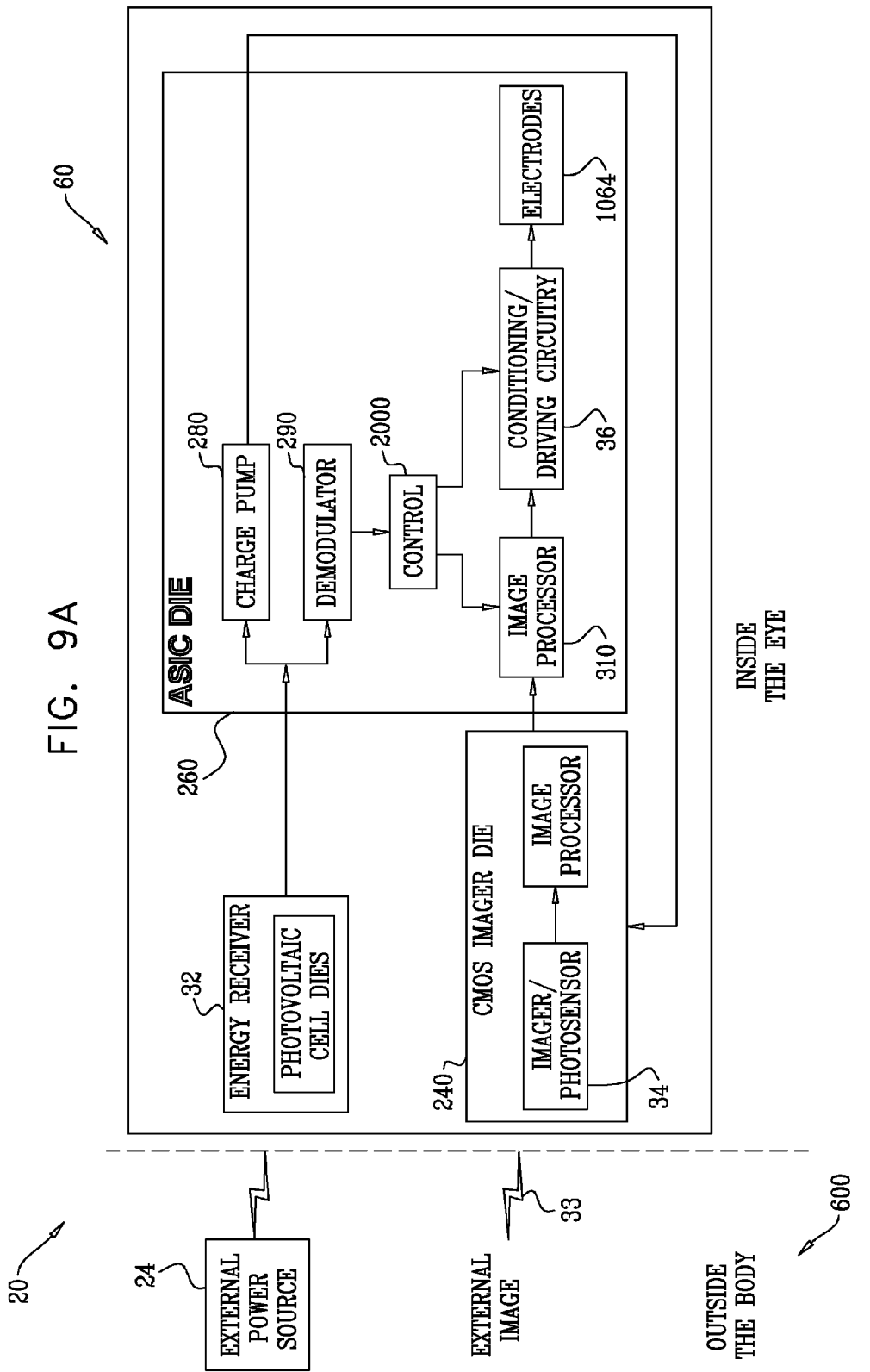
FIGS. 9A-C are schematic illustrations of the system for restoring vision, in accordance with some applications of the present invention.
Figure 9B:
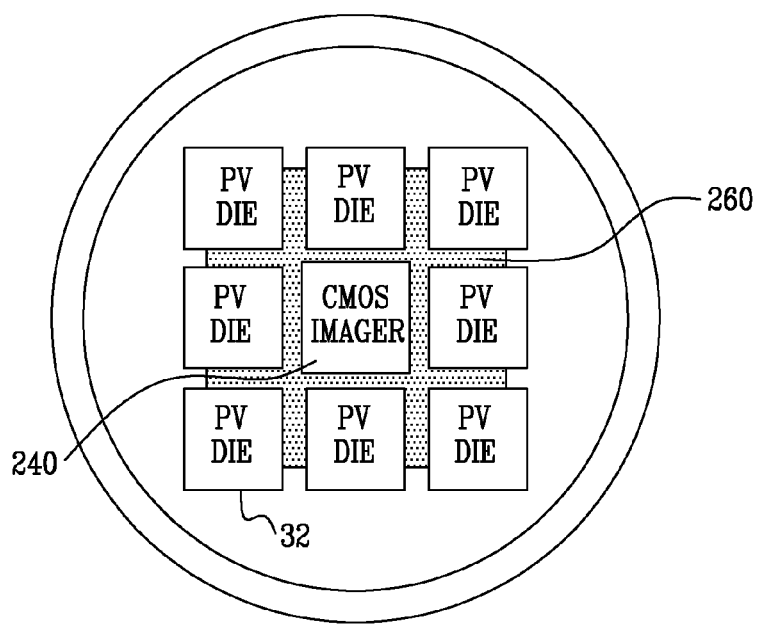
Figure 9C:
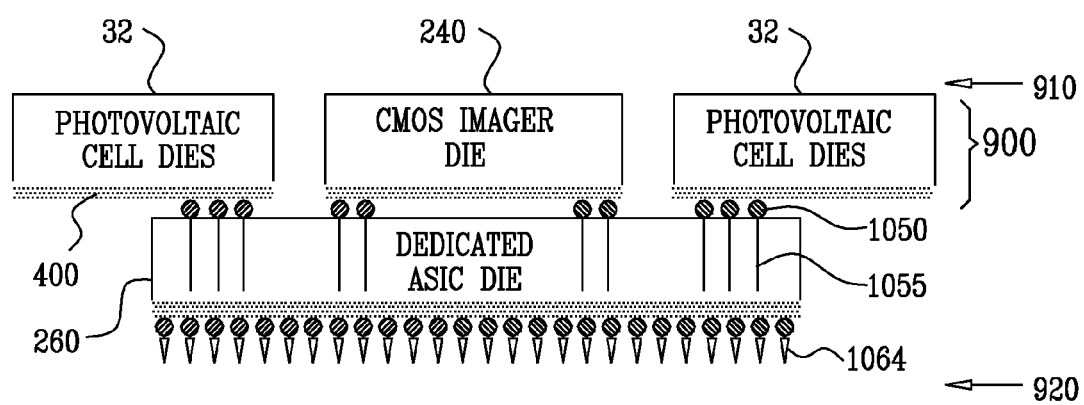

Reference is made to FIGS. 9A-C, which are schematic illustrations of system 20, in accordance with some applications of the present invention.

FIG. 9A is a block diagram of transmission of energy, information, and instructions, in the system for restoring vision, in accordance with some applications of the present invention. External device 600 is located outside of a body of a subject and comprises power source 24, which emits energy to power components of intraocular device 60. Intraocular device 60 is shown in FIG. 9A as comprising at least one energy receiving die 32, a CMOS imager die 240 and a custom-made ASIC die 260. The energy which is transmitted to device 60 is received by energy receiver 32, which typically comprises a plurality of discrete photovoltaic cell dies. Intraocular device 60 further comprises at least one array of photosensors 34, configured to detect photons 33 emanating from external objects and generate a photosensor signal responsively to the photons. Typically, the photosensors are incorporated into single CMOS imager die 240 comprising an imager and an image processor. This CMOS imager die may be similar to other low power CMOS imagers known in the art, and/or may be manufactured by companies such as Micron, OmniVision, ST, Mitsubishi and Kodak. For some applications, imager die 240 comprises between 10,000 and 5,000,000 pixels (by way of illustrations and not limitation). Typically, device 60 comprises between 1000 and 5000 stimulating electrodes.

The photosensor signal is transmitted to driving circuitry 36 which drives electrode 1064 to apply electrical charges to cells of the retina. As shown, for some applications, electrodes 1064 are coupled to a custom-made ASIC die 260. Typically, device 60 comprises a custom-made ASIC die 260 which additionally includes a charge pump 280, a demodulator 290, a control unit 2000, and an image processor 310. Energy from external power source 24 reaches energy receiver 32 and is passed via charge pump 280 to power components of intraocular device 60. The charge pump generates a higher voltage to be supplied to digital components of device 60. In addition to supplying power to components of ASIC die 260, charge pump 280 supplies power to imager die 240. Alternatively or additionally, photovoltaic cell dies of energy receiver 32 can be cascade wired, and thereby configured to increase voltage and enhance power supply to device 60. Energy from the energy receiver and charge pump is additionally passed to demodulator 290 and control unit 2000 in ASIC die 260. The demodulator typically receives modulated energy from energy receiver 32, and demodulates the energy to regulate, together with the control unit, operation of device 60 as described hereinabove with reference to FIG. 8. For other applications, software or hardware in the control unit is configured to demodulate the energy from energy receiver 32 to regulate operation of device 60 as described hereinabove. It is to be noted that techniques and apparatus described herein with reference to control unit 200 apply to control unit 2000 and vice versa, except where otherwise indicated.

ASIC die 260 further comprises an image processor 310 and is coupled to stimulating electrodes 1064 via driving circuitry 36 (including, for example, analog amplification functionality). The control unit typically regulates processing of the signal generated by photosensors 34 by image processor 310 in accordance with the now demodulated information. The processed photosensor signal is passed to driving circuitry 36, which drives stimulating electrodes 1064 to apply electrical charge to the retina of a subject.

For other applications, custom-made ASIC die 260 may, additionally to the above-mentioned components, also comprise energy receiver 32 and/or photosensors 34 or any combination thereof.

In an additional configuration, intraocular device 60 comprises custom-made ASIC die 260 and at least one photovoltaic die which comprises energy receiver 32 and photosensors 34.

Typically, ASIC die 260 comprises an integral BIT (built-in test), configured to generate an output when device 60 is implanted in an eye of a subject and transfer the output either in a wired or wireless manner, enabling calibration of device 60 after implantation. Alternatively, the output is used to calibrate device 60 prior to implantation, e.g., during manufacturing or pre-implantation processing.

Reference is now made to FIGS. 9B-C, which are schematic illustrations of a particular configuration of the components of device 60, in accordance with some applications of the present invention. FIGS. 9B-C show front and side views, respectively, of device 60 in accordance with some applications of the present invention. As shown, for some applications, the photosensors, which are configured to receive visible light, are incorporated into a single CMOS imager die. (Applications in which a plurality of CMOS imager dies are employed are not shown.) The CMOS imager die is typically surrounded by a plurality of photovoltaic dies configured to function as energy receivers 32 and receive energy from an external power source. Typically operation parameters of each photovoltaic die, e.g., the duration of an energy receiving period, is regulated by a discrete control unit coupled to each photovoltaic die. Alternatively, a central control unit regulates operation of the photovoltaic dies.

CMOS imager die 240 and energy receiving photovoltaic dies 32 are typically arranged in an array 900, which comprises the front side 910 of device 60 (the anterior side, when implanted). Typically, the imager die and the photovoltaic dies include a back side thereof, which forms the active surface 400 of these components. Solder bumps 1050 are deposited on a back side of array 900, electrically connecting array 900 to custom-made ASIC die 260 which typically includes through-silicon vias 1055. Alternatively the dies can be connected with wire bonding techniques. As shown in FIG. 9C, the ASIC die is coupled to electrodes 1064, which form the back side 920 of device 60 (the posterior side, when implanted). Typically device 60 is implanted in an eye of a subject, such that front side 910 of array 900 is facing the pupil, allowing visible light and energy from an external power source to strike array 900, and electrodes 1064 are positioned in a suitable orientation allowing the electrodes to directly contact and stimulate the tissue of the retina.

Figure 10:
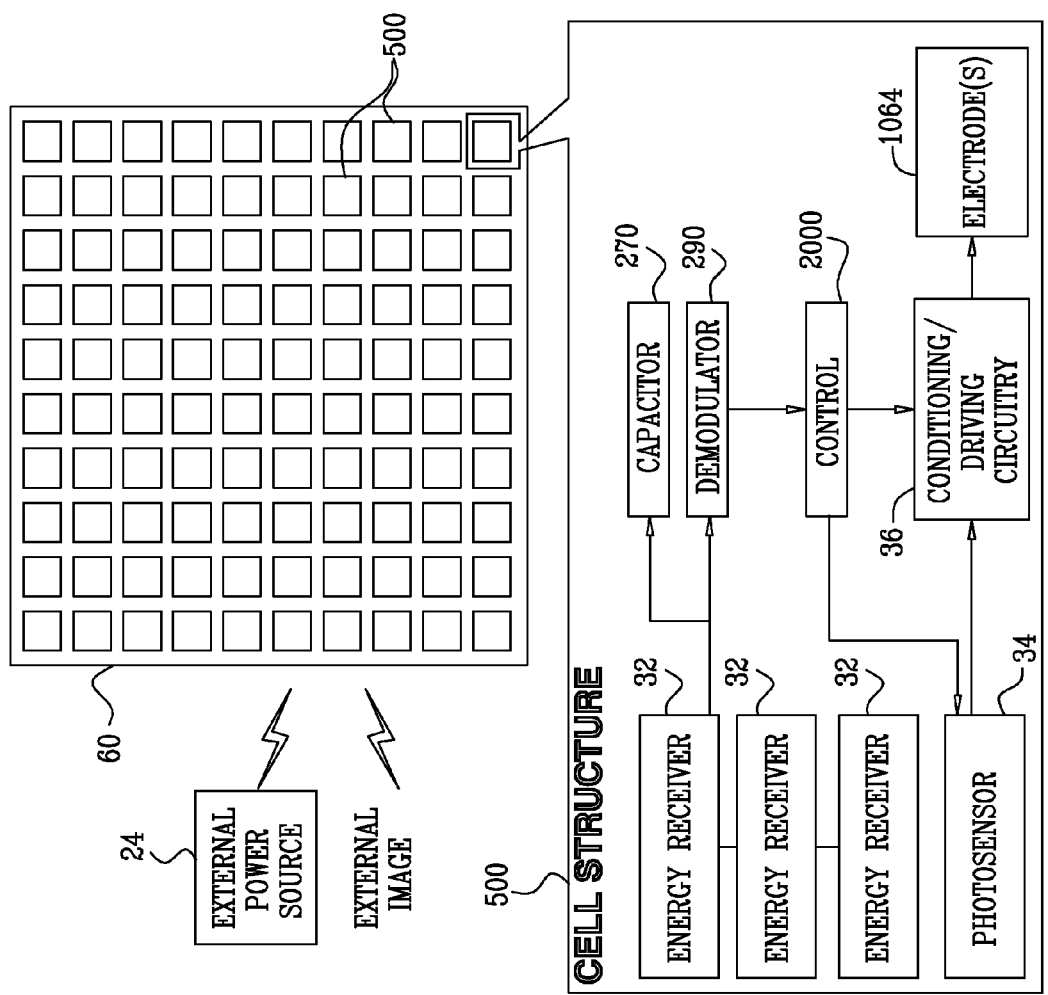
FIG. 10 is a block diagram of transmission of energy, information, and instructions, in the system for restoring vision, in accordance with some applications of the present invention.

Reference is made to FIG. 10, which is a block diagram of transmission of energy, information, and instructions, in the system for restoring vision, in accordance with some applications of the present invention. FIG. 10 shows an alternative configuration for intraocular device 60. In some applications, intraocular device 60 takes on a cellular-based configuration in which it comprises a plurality of cells, i.e., a plurality of the unit labeled 500. For some applications, intraocular device 60 comprises 1000-5000 such cells. Typically, each cell comprises an entire set of components including energy receivers 32, photosensors 34, a capacitor 270, a demodulator 290, a control unit 2000, driving circuitry 36 and 1-2 electrodes 1064. FIG. 10 shows a plurality of photovoltaic units which function as energy receivers 32 and receive energy from an external power source, e.g., a laser. For some applications, several photovoltaic units (shown in FIG. 10 as the three top photovoltaic units by way of illustration and not limitation) function as energy receivers 32, configured to receive energy from an external power source, e.g., a laser, to power the components of each cell 500. Additionally, for some applications, photosensors 34 (shown in FIG. 10 as the bottom unit by way of illustration and not limitation) are configured to receive photons emanating from an external object.

Figure 11A:
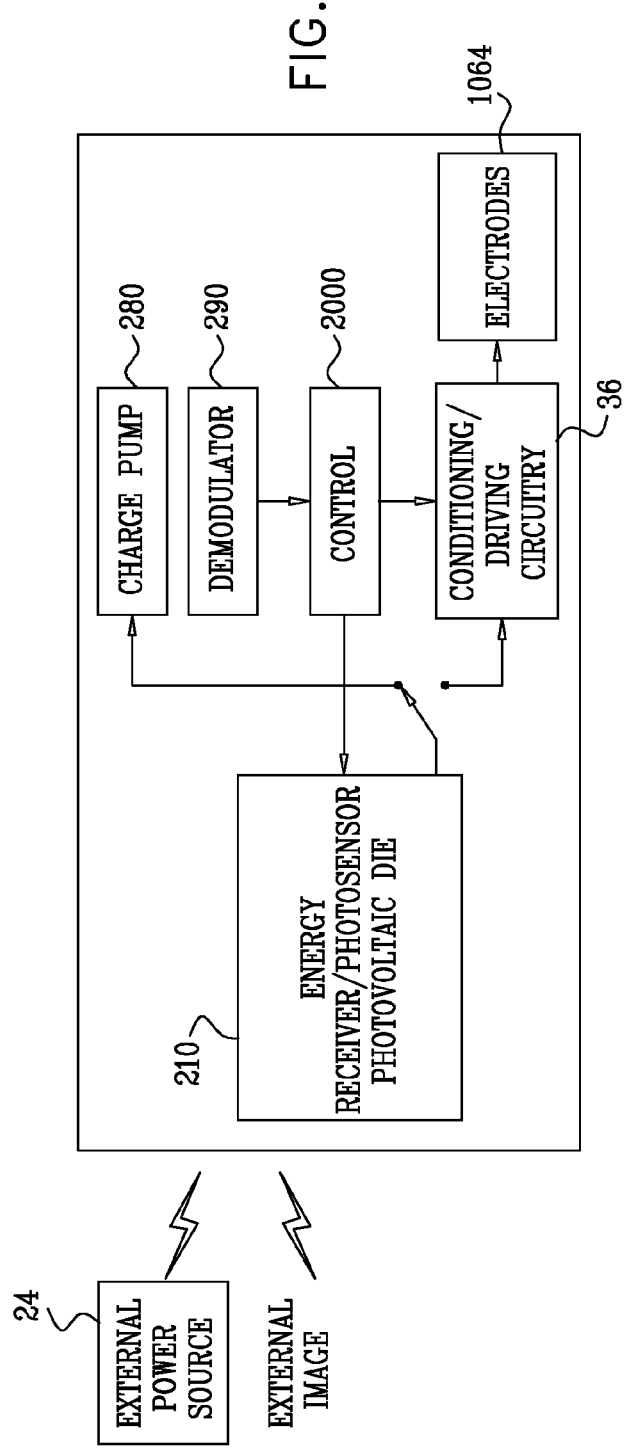
FIGS. 11A-B are block diagrams of transmission of energy, information, and instructions, in the system for restoring vision, in accordance with some applications of the present invention.
Figure 11B:
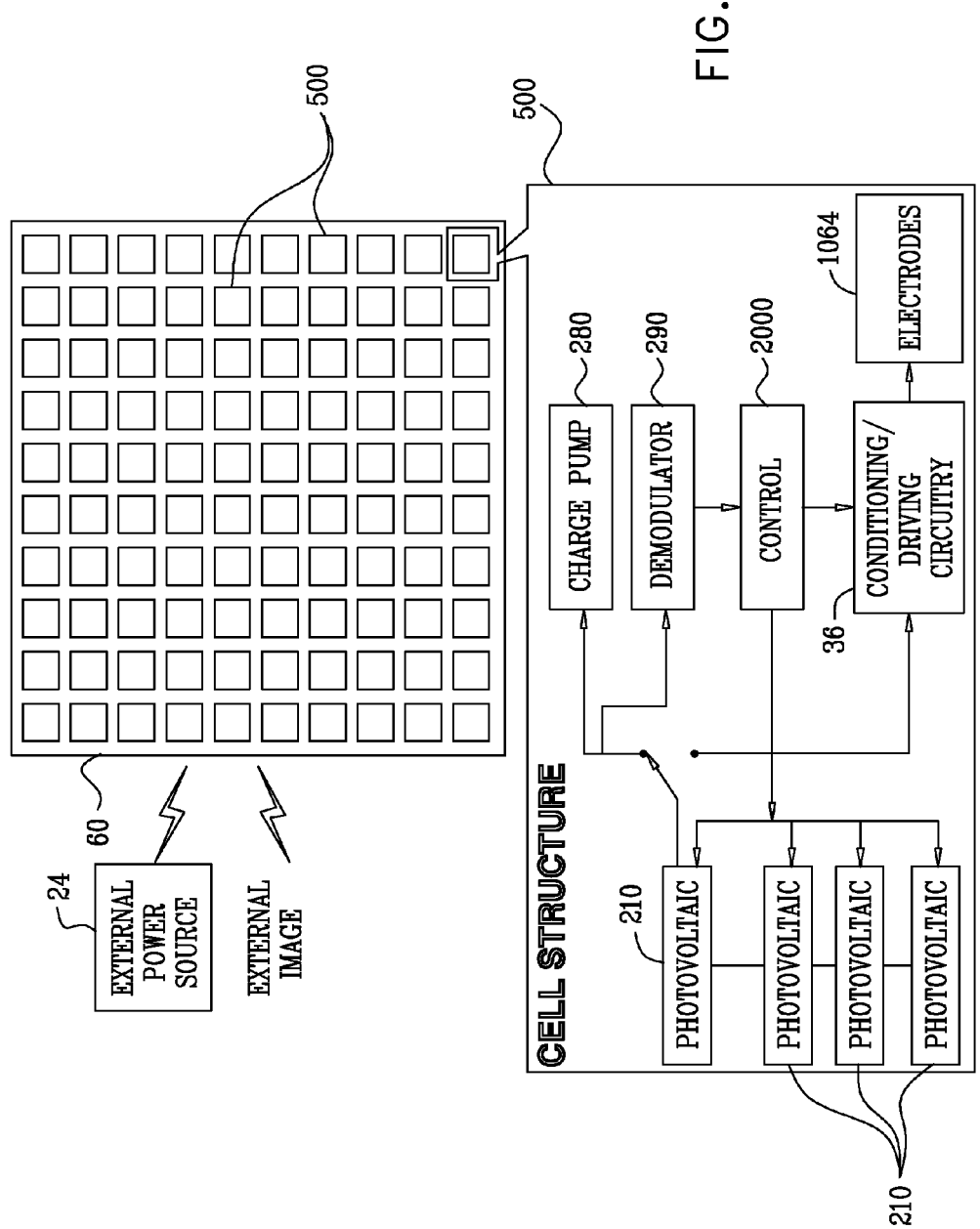

Reference is made to FIGS. 11A-B, which are block diagrams of transmission of energy, information, and instructions, in the system for restoring vision, in accordance with yet another application of the present invention. FIGS. 11A-B show external power source 24, which emits energy to power components of intraocular device 60. For some applications, a single light receiving element (indicated in FIG. 11A by box 210) functions, during alternating time periods, as an energy receiver, configured to receive energy from the external power source, and also as photosensors which are sensitive to visible light. FIG. 11A shows a central control unit 2000 which functions to regulate the operation of element 210 and to switch between energy receiving and photosensing. Central control unit 2000 further regulates the function of additional components of device 60 as described hereinabove. As shown for this application, device 60 further comprises a charge pump 280, a demodulator 290, an image processor 310 and stimulating electrodes 1064.

For some applications, intraocular device 60 comprises a plurality of fully functional cells 500 as described hereinabove with reference to FIG. 10. FIG. 11B shows a cell generally as described with reference to FIG. 10, with the distinction that each photovoltaic unit functions as both an energy receiver and a photosensor, during alternating time periods. FIG. 11B shows a plurality of light receiving elements 210 which function as energy receivers and photosensors, during alternating time periods. Typically, while functioning as an energy receiver, each component 210 receives energy to power device 60 from external power source 24. While functioning as photosensors, each element 210 is typically sensitive to ambient visible light which strikes components 210. As shown, for some applications, each cell 500 is regulated by a discrete control unit 2000 which is configured to regulate the operation of component 210 as an energy receiver and as a photosensor, during alternating time periods. Additionally, the control unit is configured to regulate switching of light receiving element 210 between energy receiving and photosensing. It is to be noted that for some applications element 210 is configured to receive other forms of energy, e.g., RF energy, to power components of intraocular device 60.

For some applications, the plurality of cells 500 are arranged in clusters of cells. Typically, the receiving of energy from the power source, and the receiving of visible light from an object, occur in two phases. For example, during a first phase, cells 500 in a cluster receive visible light and during a second phase receive energy from the power source, e.g., IR energy. The visible light received during the first phase is then used to define tissue stimulation during the second phase. Typically, the stimulation of each electrode in a given cluster occurs in sequence, in order to reduce short-term power requirements. Thus, for example, if there are four cells in a cluster, then during the second phase, each cell is actuated, in turn, to apply tissue stimulation in accordance with the light sensed by the photosensor of that cell.

Reference is made to FIGS. 9-11. Energy receivers 32 and/or photosensors 34 may comprise diodes selected from the group consisting of: a silicon diode, an amorphous silicon diode, a CMOS diode, a CMOS imaging 3-diode cell or a CMOS imaging 4-diode cell. Typically, any of these may be fabricated as back-illuminated energy receivers or photosensors, which allow passage of light through the substrate before striking the active surface. For such applications, fabrication techniques of back-illuminated sensors, which are described in one or more of the following references, are practiced in combination with techniques and device described herein: http://www.sony.net/SonyInfo/News/Press/200806/08-069E/index.html; and Swain P K., et al., in an article entitled "Back-Illuminated Image Sensors Come to the Forefront. Novel materials and fabrication methods increase quality and lower cost of sensors for machine vision and industrial imaging." Photonics Spectra August 2008.

Reference is made to FIGS. 1-11. For some applications, the electrodes described herein function to achieve biphasic stimulation of the cells. For example, the intraocular device may generate for example three voltages (e.g., 0 V, 1.5 V, and 3 V). A "ground" electrode is connected to the intermediate voltage, and a stimulation electrode is switched repeatedly between the higher voltage and the lower voltage, in order to produce biphasic stimulation. For some applications, a single voltage difference is generated (e.g., such that 0 V and 1.5 V are available) and this voltage difference is repeatedly switched to be in alternating electrical contact with two of the electrodes, so as to produce biphasic stimulation.

Reference is made to FIGS. 1-11. For some applications, a total volume of the intraocular device is less than 0.2 cc.

The scope of the present invention includes embodiments described in the following patent applications, which are incorporated herein by reference. For some applications, techniques and apparatus described in the following patent application are combined with techniques and apparatus described herein:

US Patent Application Publication 2010/0204754 to Gross, entitled, "Retinal Prosthesis," filed Feb. 9, 2009, and which issued as U.S. Pat. No. 8,150,526.

U.S. patent application Ser. No. 12/687,509 to Gefen, entitled, "Penetrating Electrodes for Retinal Stimulation," filed Jan. 14, 2010, which published as US 2011/0172736, and which issued as U.S. Pat. No. 8,718,784.

PCT Application Publication WO 2010/089739 to Gross entitled "Retinal Prosthesis," filed Feb. 3, 2010.

U.S. patent application Ser. No. 12/852,218 to Gefen, entitled, "Retinal prosthesis techniques", filed Aug. 6, 2010, which published as US 2012/0035725, and which issued as U.S. Pat. No. 8,428,740.

For some applications, techniques described herein are practiced in combination with techniques described in one or more of the references cited in the list above, as well as in the remainder of the specification, all of which are incorporated herein by reference.

The apparatus and methods described hereinbelow with reference to FIGS. 12-17B are based on the description in co-pending U.S. Ser. No. 13/148,461 (US 2012/0041514), entitled, "Retinal prosthesis," and in U.S. Ser. No. 12/368,150 (US 2010/0204754 which issued as U.S. Pat. No. 8,150,526), entitled, "Retinal prosthesis," which are incorporated herein by reference. The scope of the present invention includes utilizing the apparatus and methods of FIGS. 1-11B with the apparatus and methods of FIGS. 12-17B.

Figure 12:
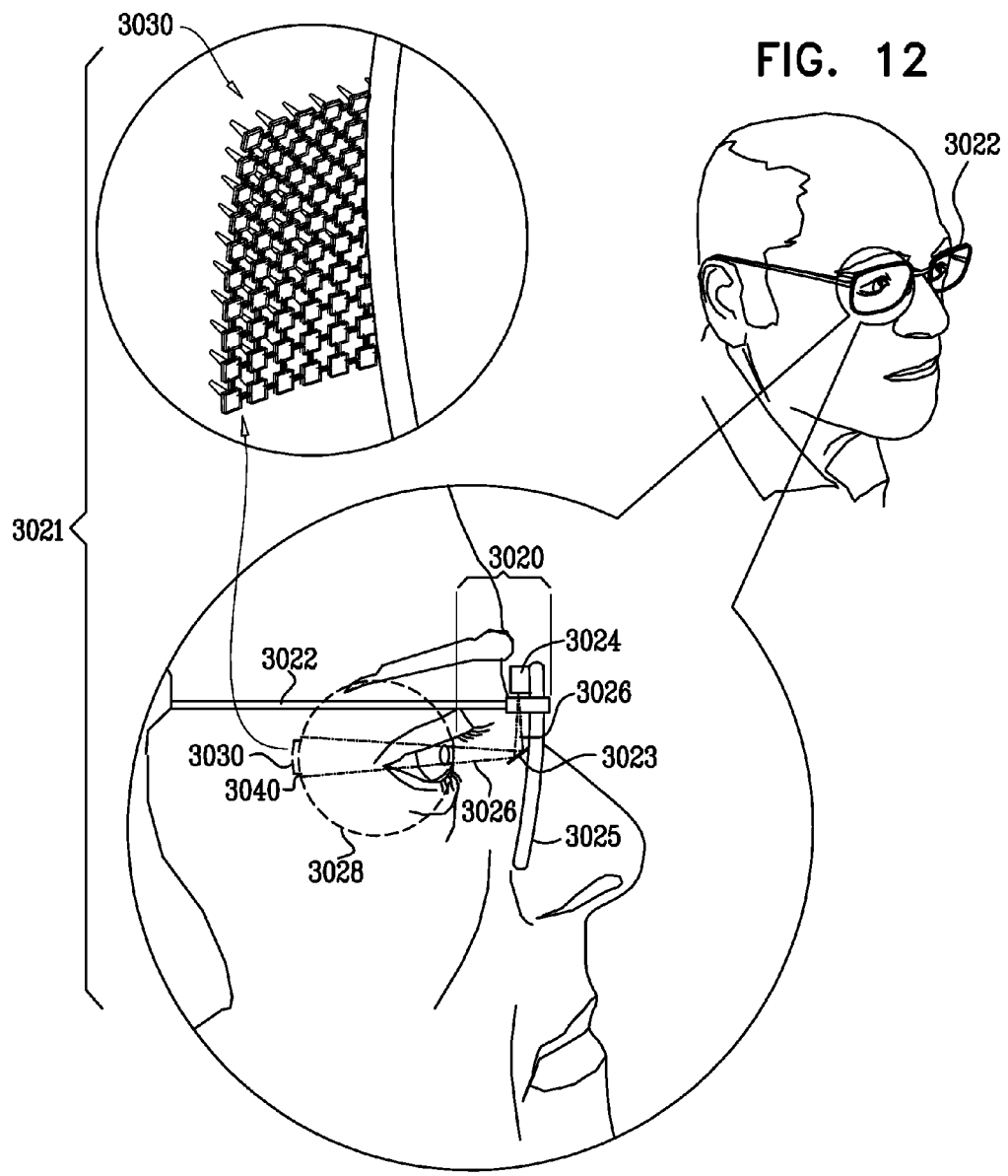
FIG. 12 is a schematic illustration of apparatus for restoring at least partial vision in a subject, in accordance with some applications of the present invention.

FIG. 12 is a schematic illustration of apparatus 3021 for restoring at least partial vision in a subject suffering from retinal malfunction, in accordance with some applications of the present invention. Apparatus 3021 comprises an external device 3020 comprising a mount 3022, which is typically a pair of eyeglasses, and is placed in front of a subject's eye 3028. External device 3020 further comprises a power source, for example a laser 3024, which is coupled to the mount and is configured to emit radiated energy 3026, which is outside the visible range, that is directed toward the subject's eye 3028. Laser 3024 is shown coupled to the inner part of lens 3025 by way of illustration and not limitation. Laser 3024 may be coupled to other members of mount 3022 for example, to the arm of the eyeglasses.

Apparatus 3021 additionally comprises an intraocular device 3030, which is implanted entirely in eye 3028. Intraocular device 3030 comprises a small e.g., 3-6 mm in diameter, thin e.g., less than 1 mm thick, and typically flexible silicon array.

Retinal implants are generally configured to be implanted in either a sub-retinal or an epi-retinal position. Epi-retinal arrays are typically implanted onto the retinal surface that separates the retinal neural layer from the vitreous body of the eye's posterior chamber. Epi-retinal implants are typically described as having no light sensitive areas and therefore receive electrical signals from a distant camera and processing unit outside of the subject's body. These described epi-retinal implants are coupled to the ganglion cells and their axons, and therefore directly simulate the ganglia (Zrenner 2002). In contrast, sub-retinal implants are typically implanted under the retina between the pigment epithelial layer and the outer layer of the retina which contains the photoreceptor cells. Sub-retinal implants typically stimulate the remaining neural cells of the retina (Zrenner 2002).

Intraocular device 3030, in accordance with some applications of the present invention, is configured to be implanted in either the epi-retinal or the sub-retinal space of eye. In both locations, intraocular device 3030 receives visible light emanating from objects. The visible light strikes photosensors of the intraocular device, which generate a signal via intermediate circuitry causing electrodes on the intraocular device to stimulate retinal sensory neurons (for example the bipolar cells), resulting in the sensation of an image. Stimulation of the bipolar cells activates and utilizes the intact optics and processing mechanisms of the eye.

In some applications of the present invention, intraocular device 3030 comprises needle electrodes with exposed tips configured to extend through the ganglion cells to directly contact and stimulate the bipolar cell layer, which in turn stimulates the ganglion cells, when intraocular device 3030 is implanted in an epi-retinal position. The ganglion cells, whose axons form the optic nerve, further transmit the visual information to the brain. Apparatus 3021 does not comprise a camera, and intraocular device does not receive image data, but rather utilizes the intact optics and processing mechanisms of eye.

In some applications of the present invention, intraocular device 3030 is implanted in the subject's eye in a sub-retinal position. As described hereinabove, intraocular device 3030 receives visible light emanating from objects. The visible light strikes the photosensors of the intraocular device, which generates a signal to drive electrodes 3038 of the intraocular device. In applications in which intraocular device 3030 is implanted in the sub-retinal space, the electrodes of intraocular device 3030 are positioned in a suitable orientation allowing the electrodes to directly contact and stimulate the bipolar cells of the retina, which in turn stimulate the ganglion cells, resulting in image resolution. Similar to the implantation of intraocular device 3030 in the epi-retinal position, implantation in the sub-retinal position also utilizes the intact optics and processing mechanisms of eye 3028.

Figure 13:
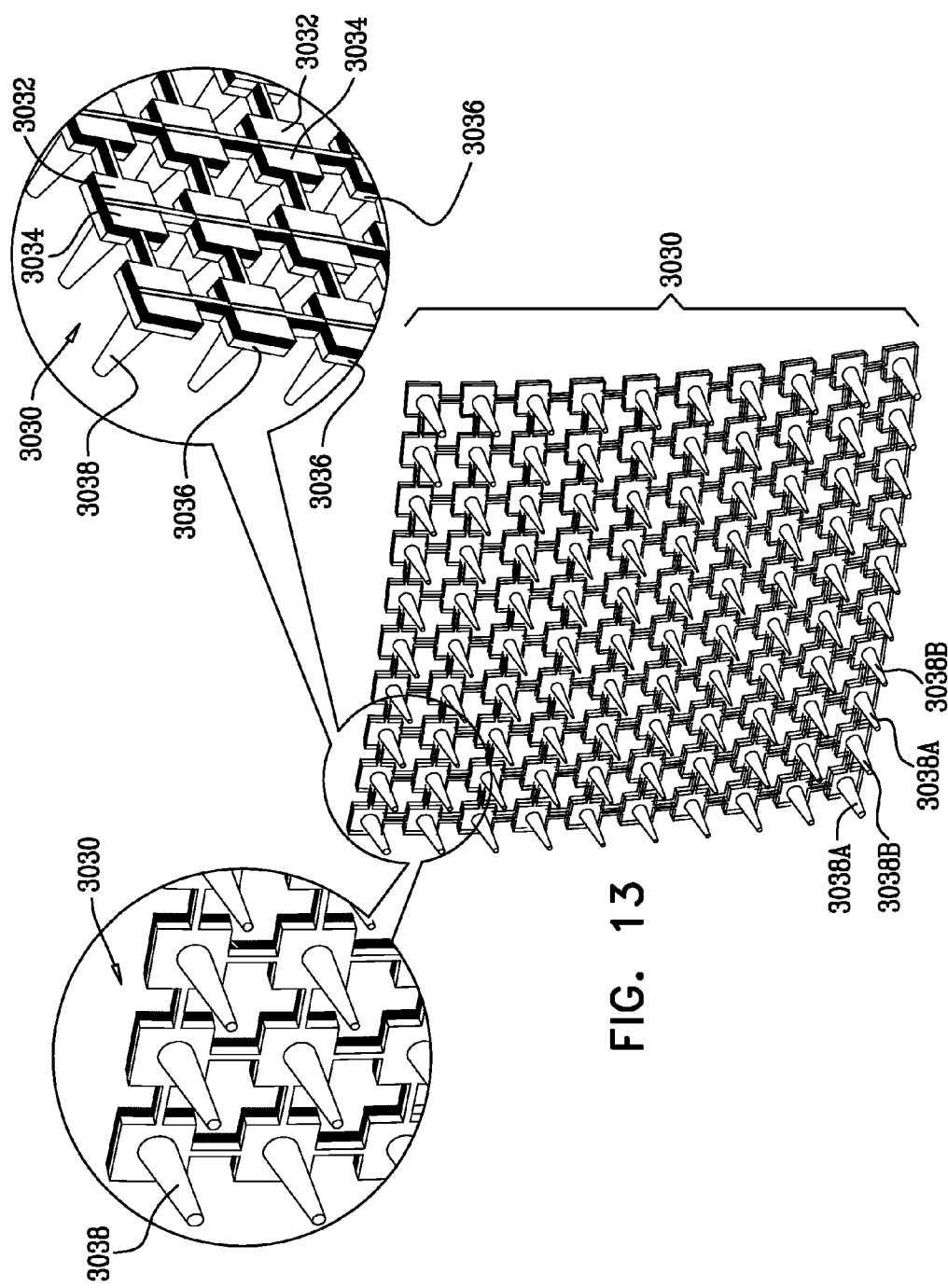
FIG. 13 is a schematic illustration of an intraocular device, in accordance with some applications of the present invention.

FIG. 13 is a schematic illustration of intraocular device 3030, in accordance with some applications of the invention. Intraocular device 3030 comprises an array, each unit of the array comprising an energy receiver 3032 which receives radiated energy 3026 from laser 3024 of external device 3020 (FIG. 12). Energy receiver 3032 generates a power signal to power other components of intraocular device 3030. Alternatively, a single energy receiver 3032 (or a small number of receivers 3032) is configured to receive radiated energy 3026 from laser 3024, to power the components of the entire intraocular device 3030. Each unit of the intraocular device 3030 further comprises a photosensor 3034, a stimulating electrode 3038, and driving circuitry 3036. A signal generated by photosensor 3034 is passed to driving circuitry 3036, which utilizes energy from the energy receiver 3032 to drive electrode 3038 to stimulate the retina. Alternatively, some or all of electrodes 3038 are driven by driving circuitry 3036 in a single area of intraocular device 3030 (rather than by discrete driving circuitry physically located next to each electrode). Accordingly, for some applications, intraocular device 3030 may comprise a plurality of driving circuitries, e.g., 10-3000 driving circuitries, each driving circuitry being configured to drive a respective subset of electrodes.

It is noted that FIG. 13 shows intraocular device 3030 configured for epi-retinal implantation. In another application, electrodes 3038 extend from intraocular device 3030 in the direction of the pupil, and intraocular device 3030 is implanted sub-retinally (configuration not shown).

Reference is now made to FIGS. 12 and 13. External device 3020 further comprises ophthalmoscope functionality, including a partially-transparent (e.g., half-silvered) mirror 3023 coupled to a lens 3025 of mount 3022. The partial transparency of mirror 3023 allows energy from laser 3024 to reach energy receiver 3032 without the physical apparatus of laser 3024 occluding vision. Additionally, light from the environment which forms images on the array of photosensors 3034 is able to pass through partially-transparent mirror 3023. The use of ophthalmoscope functionality as described further allows the use of a large diameter laser beam (e.g., 5-20 mm, such as 5-10 mm), which provide high total radiated energy 3026, while minimizing the density of the beam at the retina. If such a laser beam originated from a laser mounted on lens 3025 itself, it would interfere with vision by blocking incoming light from the environment.

Figure 14:
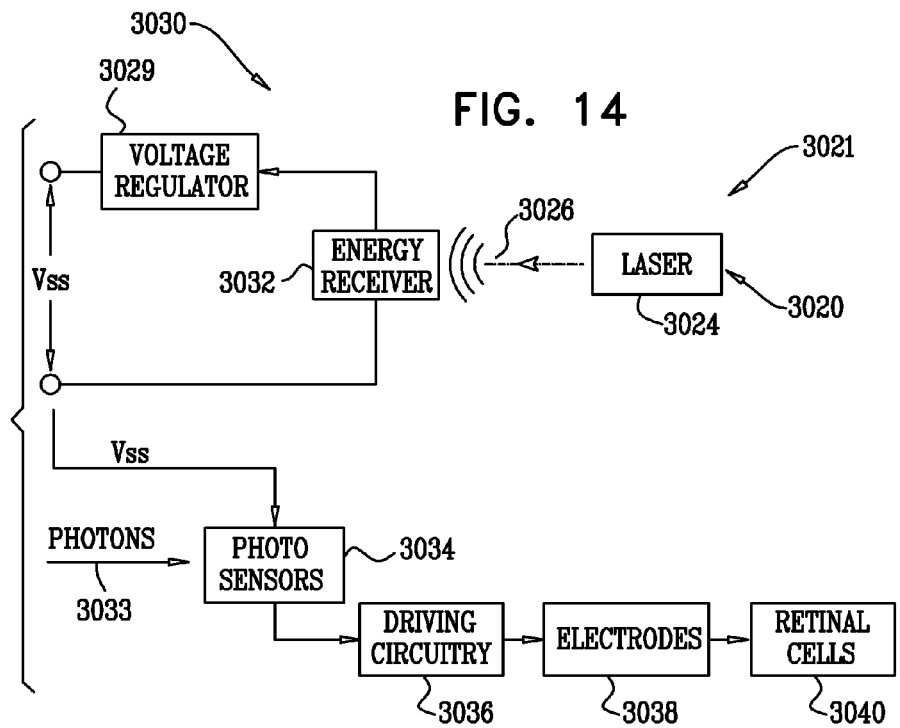
FIG. 14 is a block diagram of the transmission of energy in the apparatus for restoring vision, in accordance with some applications of the present invention.

FIG. 14 is a block diagram of apparatus 3021, in accordance with some applications of the present invention. External device 3020 (FIG. 12) comprises laser 3024, which emits radiated energy 3026 to power components of intraocular device 3030. Radiated energy 3026 transmitted to the intraocular device 3030 is received by energy receiver 3032. Energy receiver 3032 typically comprises a voltage regulator 3029 configured to maintain a constant voltage level to power the components of intraocular device 3030. Intraocular device 3030 further comprises photosensors 3034 configured to detect photons 3033 and generate a photosensor signal responsively to the photons 3033. The photosensor signal is transmitted to driving circuitry 3036, which drives the electrode 3038 to apply currents to retinal cells 3040.

Figure 15:
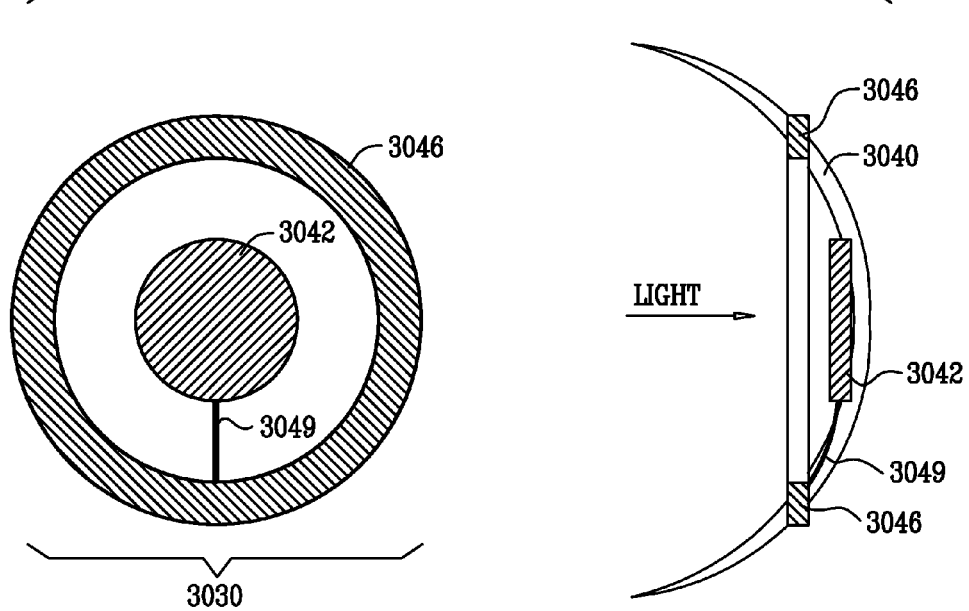
FIG. 15 is a schematic illustration of the intraocular device, in accordance with some applications of the present invention.

FIG. 15 is a schematic illustration of intraocular device 3030, in accordance with some applications of the present invention. Intraocular device 3030 comprises a generally small array 3042, e.g., 3-6 mm in diameter, and 1 mm thick. The array is surrounded by an additional toroidal array 3046 that is physically associated with the rod cells area of the retina 3040, providing some degree of scotopic vision and/or wider-field vision. Arrays 3042 and 3046, which generally function in a similar manner, are coupled by a multi-wire element 3049.

Figure 16:
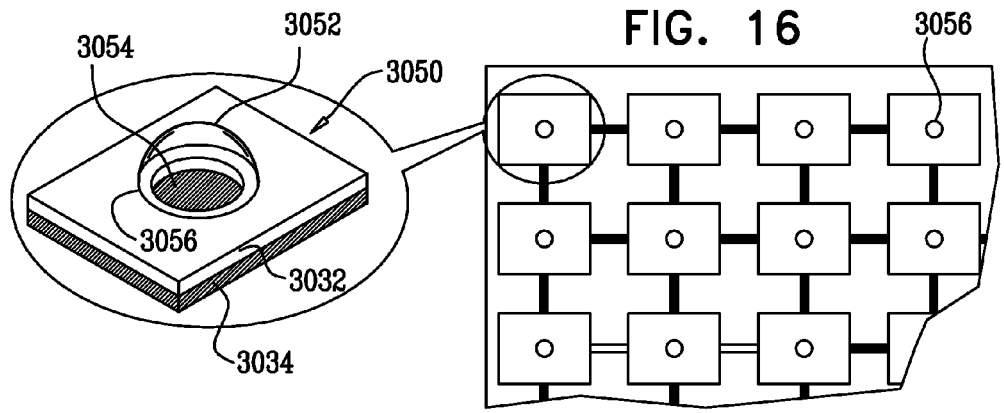
FIG. 16 is a schematic illustration of an energy receiver-photosensor unit, in accordance with some applications of the present invention.

FIG. 16 is a schematic illustration of an energy receiver-photosensor unit 3050, in accordance with some applications of the present invention. Each energy receiver 3032 has a hole 3056 passing therethrough, through which light passes to strike a corresponding photosensor 3034 located under the hole 3056. The energy-receiving portion of each energy receiver 3032 is typically 50-250 um across (e.g., 75-150 um across), and the diameter of each hole is typically 10-120 um, e.g., 20-60 um. The energy-receiving area of each energy receiver is typically about 5-10 times greater than the area of each hole.

Photosensor 3034 typically comprises a filter 3054 allowing transmission of visible light, and blocking transmission of light emitted by laser 3024. As appropriate, filter 3054 may allow substantially only visible light, or visible light and some non-visible light (e.g., near infrared) to strike the photosensor. Energy receiver 3032 is typically optimized to transduce light of the wavelength of laser 3024 into electricity, although it may alternatively be sensitive to a wider range of wavelengths, such as to both visible and non-visible light.

For some applications, energy receiver-photosensor unit 3050 comprises a microlense 3052, which facilitates refraction of light toward photosensor 3034 that would otherwise strike energy receiver 3032. Accordingly, microlense 3052 comprises prism functionality, allowing for differential refraction of visible light and non-visible (power transmitting) light, such that the non-visible light lands on the energy receiver to power intraocular device 3030, while the visible light is refracted toward photosensors 3034 which generate a signal in response to visible light photons. This provides some "averaging" of the light striking each photosensor, by combining that light with light that would otherwise strike the implant near the photosensor, thus mitigating the sensation of spaced individual pixels of light that may be sensed by a user with a retinal prosthesis. Using this technique, a slightly blurred image is intentionally formed, in which the extent of stimulation applied by a given electrode to the retina represents not only the light striking the very-small area of the corresponding photosensor, but also light that strikes the surrounding area under the microlense. (It is to be understood that in some embodiments, such a microlense is not provided.)

Figure 17A:
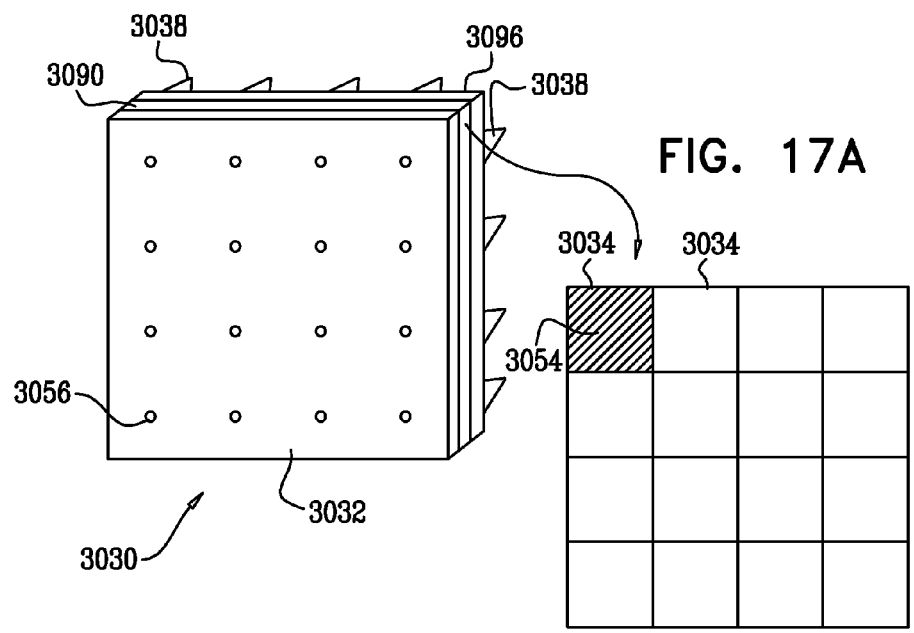
FIGS. 17A and 17B are schematic illustration of layered structures of the intraocular device, in accordance with respective applications of the invention.

Reference is made to FIG. 17A, which is a schematic illustration of intraocular device 3030, in accordance with some applications of the invention. In some embodiments of the present invention intraocular device 3030 is assembled as a triple-layered device, comprising an energy receiving 3032 top layer, a photosensor middle layer 3090 and a driving circuitry layer 3096, coupled to electrodes 3038. Energy receiving 3032 layer is configured to receive radiated laser energy, in order to power intraocular device 3030. Additionally, energy receiving 3032 layer is shaped to define a plurality of holes 3056 passing therethrough, through which light passes to strike photosensor layer 3090 located under the holes 3056. The middle layer of intraocular device 3030 comprises individual photosensor units 3034. Each photosensor unit typically comprises a filter 3054 allowing transmission of visible light, and blocking transmission of light emitted by the laser. Visible light striking photosensor units 3034 generates a current which is processed in the bottom, driving circuitry layer 3096, of intraocular device 3030. Driving circuitry layer 3096 is coupled to electrodes 3038 that stimulate the retinal cells to generate an image and restore vision.

It is noted that FIG. 17A shows intraocular device 3030 configured for epi-retinal implantation. In another application, electrodes 3038 extend from the energy receiving 3032 layer, and intraocular device 3030 is implanted sub-retinally (configuration not shown).

Figure 17B:
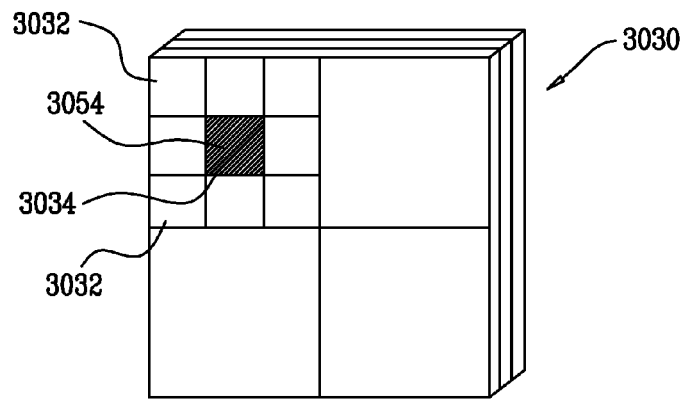

Reference is made to FIG. 17B, which is a schematic illustration of intraocular device 3030, in accordance with another application of the invention. In this application, the top layer of intraocular device 3030 comprises both energy receivers 3032 and photosensors 3034. For example, the top layer of intraocular device 3030 may comprise an array divided into sub-arrays. Each sub-array is further divided into (for example) nine units each. The central unit of each sub-array comprises a photosensor 3034, typically comprising a filter 3054 which passes visible light. The surrounding units in each sub-array are energy receiving units 3032, receiving radiated laser energy to power intraocular device 3030. As appropriate, electrodes 3038 may be coupled to the top layer, for sub-retinal implantation, or to the bottom layer, for epi-retinal implantation.

Typically, apparatus 3021 activates and utilizes the intact optic mechanisms, natural movements, and focusing of eye 3028. Furthermore, intraocular device 3030 is typically a small and flexible device e.g., 3-6 mm in diameter, and less than 1 mm thick, implanted in a either an epi-retinal or a sub-retinal position, and powered by an external power source e.g., a laser. Therefore, intraocular device 3030 is wireless, does not comprise bulky components, and does not require power-consuming internal microcontrollers. Additionally, energy receiver 3032, receiving radiated energy 3026, for example laser energy, is typically fine-tuned to match a specific laser wavelength (for example an IR wavelength such as 790-850 nm, or a suitable UV wavelength). Therefore, a substantial portion of radiated energy 3026 is utilized to power electrodes 3038, allowing for an increased number of electrodes 3038 and thereby resulting in enhanced image resolution. For example, if a total of 35 mW of laser energy reaches intraocular device 3030, this provides an estimated 14 mW of usable electricity (assuming an approximate 40% efficiency rate).

For some applications electrodes 3038 are bipolar or alternatively monopolar nanotube electrodes coated with carbon nanotubes.

The number of electrodes per array typically ranges between 100-10,000 electrodes. In some applications, a relatively smaller number of electrodes (e.g., 100-1,000) are in generally continuous use, while a higher number of electrodes (e.g., 1,000-10,000), which are not continuously activated, can enable the subject to temporarily increase resolution at the cost of heating of the eye for several seconds. Additionally or alternatively, intraocular device 3030 comprises interleaved arrays of electrodes 3038*a* and 3038*b*, which are activated separately, thus stimulating adjacent retinal sites and generating the illusion of higher-resolution of an actual image.

In some applications of the present invention, intraocular device 3030 comprises support elements extending away from the retina. Support elements are typically composed of biocompatible materials (for example, PtIr), possibly insulated with an additional biocompatible material. The support elements aid in anchoring implanted intraocular device 3030 to the subject's eye 3028. Additionally or alternatively, the support elements contribute to enhanced dissipation of heat, preventing local overheating of eye 3028. The total volume of support elements is typically similar to the volume of intraocular device 3030 (for example, 25 mm3), allowing for efficient heat dissipation.

In some applications of the present invention, external device 3020 comprises a sensor coupled to mount 3022. Apparatus 3021 is configured to detect blinking, and to not transmit power to intraocular device 3030 when the subject's eyelid is closed. The sensor is configured to detect the rapid closing and opening of the eyelid of the subject, and to signal to laser 3024 to cease emitting radiation 3026 to the eye when the eyelid of the subject is closed. For some applications, the sensor comprises an electromyography (EMG) sensor or a camera with image processing functionality to determine when the eye is closed. For some applications, the sensor comprises a light sensor coupled to a light emitting diode (LED), which is located adjacent to laser 3024. The LED emits light which passes through partially-transparent mirror 3023 and is directed towards the subject's eye 3028. The amount (or another parameter) of reflected LED light from the eye changes as a result of the subject's blinking. These changes in the amount of the reflected light are detected by the light sensor, which causes laser 3024 to discontinue emitting radiation 3026 to eye 3028 when the eyelid of the subject is closed. Alternatively, for some applications, mount 3022 comprises a light sensor located in proximity to laser 3024. The light sensor detects reflected laser light, and laser 3024 discontinues emitting radiation 3026 to the eye when the eyelid of the subject is closed.

In some embodiments of the present invention, apparatus 3021 is configured to provide the subject with audio feedback advising the subject to aim eye 3028 so that radiation from laser 3024 reaches intraocular device 3030. Accordingly, for some applications, external device 3020 comprises a light sensor coupled to laser 3024, configured to detect the amount of reflected laser light and to trigger an audio signal to the subject based on changes in the reflected light indicative of the laser light not being directed toward intraocular device 3030. For example, a different portion of the laser light is absorbed by intraocular device 3030 when laser 3024 is properly aimed, compared to when the laser beam is diverted and not directed at eye 3028. In this latter case, the audio feedback signal is triggered.

For some applications, in addition to supplying power to device 3030, radiation 3026 emitted by laser 3024 is used to regulate operation of intraocular device 3030. In some applications of the present invention, external device 3020 comprises a control element (e.g., a dial, switch, or button) coupled to mount 3022, allowing the subject to interactively control the intensity of the signal applied to the retina and/or the sensitivity of photosensors 3034 to received light, and/or another system parameter. For example, if the subject determines that the overall stimulation being applied by intraocular device 3030 to the retina is too strong, then he can adjust a setting on the control element to reduce the stimulation strength. Similarly, if he determines that the sensitivity of photosensors 3034 is too high (e.g., resulting in the entire array of electrodes activating the retina), then he can adjust another setting on the control element to reduce the sensitivity. In response to the subject's input, control element 3027 modulates radiation 3026 emitted by laser 3024 to regulate operating parameters of intraocular device 3030. An example of a suitable modulation protocol includes a first train of six short pulses from laser 3024, indicating that stimulation intensity is going to be changed, followed by a train of between one and ten longer pulses indicating a subject-selected desired level of stimulation intensity. To change sensitivity, a first train of six long pulses is emitted from laser 3024, followed by a train of between one and ten longer pulses indicating a subject-selected desired level of sensitivity. A person of ordinary skill in the art will appreciate that other encoding protocols may be used, as well.

Alternatively, for some applications, regulation of the intensity of the signal applied to the retina and/or the sensitivity of photosensors 3034 to received light, and/or another system parameter, is regulated by intraocular device 3030. The degree of retinal stimulation applied by each unit of intraocular device 3030 is dictated by the light received by that unit. Intraocular device 3030 is configured to sense the amount of ambient light which is received by photosensors 3034, and in response, to alter the signal which is applied to the retina. For example, based on the amount of ambient light which lands on a given photosensor, intraocular device 3030 is configured to modulate the signal by adjusting photosensor output and/or driving circuitry parameters such as gain and/or DC offset, allowing for increased sensitivity of apparatus 3021. Modulation of the signal applied to the retina is typically controlled by varying pulse parameters, e.g., of number of pulses, pulse repetition intervals, pulse frequency, and pulse duration. That is, electrodes 3038 drive currents into the retinal neurons using pulse parameters selected in response to the amount of light received by the photosensor. Such modulation of photosensor pulse signals to the driving circuitry facilitates regulation of intraocular device 3030, for example, in response to changing levels of ambient light.

Similarly, the threshold for transmission of a photosensor signal to the driving circuitry i.e., the sensitivity of photosensors 3034, is regulated by the amount of ambient light reaching the photosensors. For some applications, the amount of ambient light that lands on the array of photosensors 3034 is used to govern the duration of a sensing period of each photosensor, i.e., the amount of time in which the photosensor receives photons before the driving circuitry drives electrodes 3038 to drive currents into retinal tissue (e.g., 10 ms-100 ms). Thus, for example, the sensitivity of each photosensor may be increased over the course of several seconds, if the subject enters a dark room.

Typically, regulation of system parameters of intraocular device 3030, by laser and/or by device 3030 itself, is achieved by varying selected pulse parameters, e.g., the number of pulses, pulse repetition intervals, pulse frequency, and/or pulse duration.

As described hereinabove, in addition to powering intraocular device 3030, in some applications, radiation 3026 emitted by laser 3024 is additionally used to regulate operating parameters of intraocular device 3030. Laser 3024 is typically configured to emit energy 3026 that is outside the visible range and is directed toward the subject's eye 3028. For example, the radiation may be infrared (IR) radiation. For such applications, lens 3025 of eyeglasses 3022 may comprise an optical filter, e.g., a Schott filter. The filter is configured to filter IR radiation, thereby reducing the amount of ambient IR radiation that reaches photosensors 3034 and may interfere with the IR radiation emitted by laser 3024. Radiated energy 3026 is generally not affected by the filter placed on lens 3025, as laser 3024 is typically coupled to the inner part of lens 3025 as shown in FIG. 12.

In some applications of the present invention, activation of apparatus 3021 is regulated by a threshold to prevent saturation (i.e., over-stimulation of the retina by intraocular device 3030).

It is to be noted that a plurality of intraocular devices 3030 may be implanted in discrete locations in tissue of the retina, either arranged in an array, or, for example, pseudo-randomly. Typically, intraocular device 3030 is wireless and does not comprise bulky components, facilitating implantation of several intraocular devices 3030 in the retina of a subject.

For some applications, techniques described herein are practiced in combination with techniques described in one or more of the following references, which are incorporated herein by reference:

U.S. Pat. No. 4,628,933 to Michelson
U.S. Pat. No. 5,597,381 to Rizzo
U.S. Pat. No. 5,935,155 to Humayun et al.
U.S. Pat. No. 6,298,270 to Nisch
U.S. Pat. No. 6,324,429 to Shire et al.
U.S. Pat. No. 6,368,349 to Wyatt et al.
U.S. Pat. No. 6,507,758 to Greenberg et al.
U.S. Pat. No. 6,976,998 to Rizzo et al.
U.S. Pat. No. 7,047,080 to Palanker et al.
US Patent Application Publication 2006/0282128 to Tai et al.
US patent Application Publication US 2007/0191909 to Ameri et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
an extraocular device comprising:
eyeglasses, configured to be placed in front of an eye of a subject; and
a power source coupled to the eyeglasses and configured to emit a beam of light that is outside of 380-750 nm, the power source being arranged with respect to the eyeglasses such that reflection of the beam of light causes a diverging beam of the light to leave the apparatus and diverge as it enters the eye; and
an intraocular device configured to be implanted entirely in the subject's eye in an epi-retinal position, comprising:
an energy receiver, configured to receive the beam of light from the power source and to generate a voltage drop in response thereto;
a plurality of stimulating electrodes;
a plurality of photosensors, each photosensor configured to detect photons and to generate a signal in response thereto; and
driving circuitry, coupled to the energy receiver and to the photosensors, and configured to receive the signals from the photosensors and to utilize the voltage drop to drive the electrodes to apply currents to a retina of the eye in response to the signals from the photosensors.

2. The apparatus according to claim 1, further comprising a mirror coupled to the eyeglasses, and configured to reflect the beam of light to cause a diverging beam of the light to enter the eye.

3. The apparatus according to claim 2, wherein the mirror comprises a partially-transparent mirror.

4. The apparatus according to claim 3, wherein the partially-transparent mirror is configured to allow ambient light to pass through to the eye.

5. The apparatus according to claim 2, wherein the mirror comprises a dichroic mirror.

6. The apparatus according to claim 2, wherein the eyeglasses comprise an eyeglass lens, and wherein the mirror is coupled to the eyeglass lens of the eyeglasses.

7. The apparatus according to claim 2, wherein the eyeglasses comprise an eyeglass lens, and wherein the mirror is configured to be disposed between the eyeglass lens and the eye of the subject when the subject is wearing the eyeglasses.

8. The apparatus according to claim 1, wherein the eyeglasses comprise an arm of the eyeglasses, and wherein the power source is attached to the arm of the eyeglasses.

9. The apparatus according to claim 1, wherein an angle of divergence of the diverging beam is 8 degrees.

10. The apparatus according to claim 1, wherein the extraocular device further comprises a partially-transparent mirror coupled to the eyeglasses and wherein the partially-transparent mirror is configured to direct the diverging beam of light from the power source to the intraocular device.

11. A method for powering a retinal intraocular implant, implanted in an epi-retinal position, the implant including an energy receiver and a plurality of photosensors configured to receive an ambient image through a lens of the eye, the method comprising:
emitting a beam of light, from a power source attached to eyeglasses, in a direction that is not toward the retinal implant;
powering the retinal implant by reflecting the beam as a diverging beam of light and conveying the diverging beam of light toward the implant;
receiving the ambient image through the lens of the eye, by the plurality of photosensors of the implant; and
powering the photosensors with power extracted from the diverging beam by the energy receiver.

12. The method according to claim 11, wherein reflecting the beam of light comprises reflecting the beam of light by a partially-transparent mirror.

13. The method according to claim 12, further comprising:
receiving, by the retinal implant, the diverging beam of light reflected by the partially-transparent mirror; and receiving, by the retinal implant, ambient light that passes through the partially-transparent mirror.

* * * * *